US006409764B1

(12) United States Patent
White et al.

(10) Patent No.: US 6,409,764 B1
(45) Date of Patent: Jun. 25, 2002

(54) METHODS AND ARTICLES FOR REGENERATING BONE OR PERIDONTAL TISSUE

(76) Inventors: Charles F. White, P.O. Box 825, Camp Verde, AZ (US) 86322; Charles Flynn, 740 E. Mingus Ave., Apt. 2039, Cottonwood, AZ (US) 86326; Alonzo D. Cook, 1665 W. University Heights Dr. S.; William R. Hardwick, 41 Pine Cone Dr., both of Flagstaff, AZ (US) 86001; Ulf M. E. Wikesjo, 518 Morris Ave., Bryn Mawr, PA (US) 19010; Robert C. Thomson, 623 N. Leroux St., Flagstaff, AZ (US) 86001

( * ) Notice: Subject to any disclaimer, the term of this patent is extended or adjusted under 35 U.S.C. 154(b) by 0 days.

(21) Appl. No.: 09/205,150

(22) Filed: Dec. 3, 1998

(51) Int. Cl.⁷ .............................. A61F 2/28; A61C 13/00
(52) U.S. Cl. .................................. 623/16.11; 623/23.72; 623/23.76; 623/901; 424/424; 433/201.1; 433/215
(58) Field of Search ........................... 623/16.11, 23.58, 623/23.72, 23.75, 23.76, 901; 433/215, 201.1; 424/424

(56) References Cited

U.S. PATENT DOCUMENTS

| | | | |
|---|---|---|---|
| 4,787,906 A | 11/1988 | Haris | 623/16 |
| 5,032,445 A | 7/1991 | Scantlebury et al. | 428/158 |
| 5,059,123 A | 10/1991 | Jernberg | 433/215 |
| 5,077,049 A | 12/1991 | Dunn et al. | 424/426 |
| 5,197,882 A | 3/1993 | Jernberg | 433/215 |
| 5,211,664 A | 5/1993 | Tepic et al. | 623/16 |
| 5,219,576 A | 6/1993 | Chu et al. | 424/484 |
| 5,354,557 A | 10/1994 | Oppermann et al. | 424/423 |
| 5,383,931 A | 1/1995 | Hehli et al. | 623/16 |
| 5,433,996 A * | 7/1995 | Kranzler et al. | 428/247 |
| 5,466,262 A | 11/1995 | Saffran | 623/16 |
| 5,470,829 A * | 11/1995 | Prisell et al. | 514/12 |
| 5,569,308 A | 10/1996 | Sottosanti | 623/165 |
| 5,676,699 A | 10/1997 | Gogolewski et al. | 623/16 |
| 5,683,459 A | 11/1997 | Brekke | 623/16 |
| 5,906,934 A * | 5/1999 | Grande et al. | 435/325 |
| 5,919,234 A * | 7/1999 | Lemperle et al. | 623/16 |
| 5,942,437 A * | 8/1999 | Sanberg et al. | 435/374 |

FOREIGN PATENT DOCUMENTS

| | | |
|---|---|---|
| DE | 19741395 A1 | 4/1999 |
| EP | 0 551 611 B1 | 2/1996 |
| EP | 0 475 077 B1 | 6/1996 |
| WO | WO 98/07384 | 2/1998 |

OTHER PUBLICATIONS

Bessho, "Ectoic Osteoinductive Difference Between Urified Bovine and Recombinant Human Bone Morphogenetic Protein" Academic Press, Bone Morphogenetic Proteins: Biology, Biochemistry and Reconstructive Surgery, Chapter 10, 1996.

(List continued on next page.)

*Primary Examiner*—Corrine McDermott
*Assistant Examiner*—Choon P. Koh

(57) ABSTRACT

There are numerous medical situations involving deficiencies of living bone or periodontal tissue and where increase of living bone or periodontal tissue mass is desired. Methods are described wherein a configured, shell-like device that is capable of being penetrated by living cells and tissues, is implanted into the body of a mammal in such a way as to establish a space, the space being at least partly, bounded by the device. The configuration of the device is such that the configuration of the established space is essentially the same as the configuration of living bone or periodontal tissue that is desired for treatment of the tissue deficiency. At least one protein from the Transforming Growth Factor-Beta Superfamily of proteins is placed within the established space for the purpose of stimulating the growth of living bone or periodontal tissue within the established space. A kit for the generation of living bone or periodontal tissue, comprised of the components mentioned above, is also disclosed.

65 Claims, 14 Drawing Sheets

OTHER PUBLICATIONS

Boyne, "Animal studies of the Application of rhBMP–2 in Maxillofacial Reconstruction", Bone 19:83S–92S (1996).

Cochran, et al., "Radiographic Analysis of Regenerated Bone Around Endosseous Implants in the Canine Using Recombinant Human Bone Morphogenetic Protein–2", The International Journal of Oral & Maxillofacial Implants 12(6):739–748 (1997).

Khouri, et al., "Tissue Transformation into Bone In Vivo", JAMA 266 (14):1953–1955 (1991).

Lemperle, et al., "Comparison of Protected Bone Regeneration, Osteoconduction with Coralline Hydroxyapatite Implants, and Cancellous Bone Autografts in Large Cranial and Mandibular Defects in Dogs." Surgical Forum Plactic Surgery, pp. 723–727.

Hedner, et al., "Efficacy of Bone Morphogenetic Protein (BMP) with Osteopromotive Membranes—An Experimental Study in Rat Mandibular Defects." Eur. J. Oral Sci. 103:236–241 (1995).

Pineda, et al., "Bone Regeneration with Resorbable Polymeric Membranes. III. Effect of Poly(L–Lactide) Membrane Pore Size on the Bone Healing Process in Large Defects." J. Biomedical Materials Research, 31:385–394 (1996).

Spector, "Ceramic Materials and Bone Regeneration", Bone Symposium '91, Oregon Health Sciences University, pp. 335–350.

Holmes, et al., "A MacroPorous Protective Sheet for Bone Regeneration and Implant Containment." Orthopaedic Biomaterials, IBC's First Annual International Conference, Dec. 11–12, 1997, San Diego, California (1997).

Teixeira, et al., "Bone Morphogenetic Protein Induced Repair of Compartmentalized Segmental Diaphyseal Defects", Arch. Orthop. Trauma Surg 117:27–34 (1998).

Gugala et al., "Regeneration of Bone in Large Segmental Diaphyseal Defects Using Tube–in–tube Resorable Polymeric Implants", 23rd Annual Meeting of the Society for Biomaterials, pp. 240, Apr. 30–May 4, 1997.

Gerber et al., "Treatment of Large Diaphyseal Bone Defects Using Polylactide Membrane in Combination with Autogeneic Cancellous Bone", Fifth World Biomaterials Congress, pp. 32, May 29–Jun. 2, 1996.

Wolfe, et al., "Use of Osteoinductive Implants in the Treatment of Bone Defects", Med. Progress through Tech. 20:155–168 (1994).

* cited by examiner

Test - TP+ACS+BMP

Control - ACS+BMP

METHODS AND ARTICLES FOR REGENERATING BONE OR PERIDONTAL TISSUE

BACKGROUND

Current therapeutic options to increase bone or periodontal tissue mass are surgically complex and have several drawbacks. These options include the use of autografts, allografts, xenografts and alloplastic materials. Autografts involve the transfer of bone from one part of the patient to another (either as a vascularized graft or as a non-vascularized graft). The main drawbacks of therapies utilizing autograft bone are; the limited amount of tissue that is available for transfer, donor site morbidity and, in some cases, the complete lack of available or appropriate donor sites. In addition, in the case of non-vascularized bone grafts, resorption of the transferred tissue can result in decreased tissue mass and inadequate function and/or aesthetic outcome.

When autograft bone is not available, allografts may often be used. Allografting involves the transfer of bone between two individuals of the same species. Such procedures are not without problems however. Associated problems with this technique may include lack of donors, immunological response of the host, revitalization of the grafted material by the host, and the possibility of disease transfer from donor tissue to the recipient. Allograft bone is often highly processed to remove the mineral components and prevent immune rejection. Highly processed xenograft bone, usually of bovine origin, is sometimes used but the quality of the regenerated bone and the host immunological response are both areas for further improvement.

Much attention has been paid to the possibilities of generating or regenerating bone. Since bone has some potential for self-regeneration, porous matrices, which are usually biodegradable, have been used to direct the formation of new bone tissue. However, these regenerative processes are dependent on, and limited by, both device design and the regenerative potential inherent in the biological processes of the individual. This dependence may affect rate of formation, quantity and architecture of the resulting bone tissue. Porous materials, such as coralline hydroxyapatite and certain preparations of allograft bone, have been used as scaffolds to facilitate tissue growth into bony defects. This approach has been successful in instances associated with small defects but lacks the desired predictability of outcome in many clinically relevant large defects. Interaction of the host cells, e.g. the so called foreign body reaction, with the porous matrix also may limit the rate, quantity and architecture of the bone formed within the device.

Recent research has also focused on the use of bioactive molecules or transplanted cells that have the potential to stimulate bone formation. The local administration of cells or bioactive molecules alone is insufficient and does not result in predictable bone regeneration (Bessho 1996). Research efforts have therefore focused on the use of carriers to deliver bioactive molecules or act as scaffolds for transplanted cells. In addition the carriers act as scaffolds to direct cell growth and tissue formation. Such carriers usually take the form of space filling devices, such as three-dimensional porous networks, gels, microspheres or granular materials. Membranes which create and maintain a space for bone or periodontal tissue regeneration have also been used as carriers for bioactive molecules.

Space filling devices have been used extensively in the field of bone regeneration to act as carriers for bioactive molecules known to stimulate bone formation (Wolfe and Cook, 1994). The materials used to fill a space where bone formation is required vary widely in their structural geometry and mechanical properties and include porous hydroxyapatite, allograft bone, collagen sponge and degradable polymer foams, scaffolds (Brekke, U.S. Pat. No. 5,683,459) and microspheres. These various approaches to bone regeneration each suffer one or more drawbacks.

For example, relatively strong and rigid materials, such as porous coralline hydroxyapatite, can withstand the forces created by surrounding soft tissue, wound contracture and local load induced stresses. These materials have the capacity to resist collapse of the geometric form defined by the material and thus maintain the original shape of the space occupied by the porous matrix. However, these materials also take up a significant portion of the space which could otherwise be occupied by newly formed bone. As a consequence, such materials interfere with bone formation and also result in a potentially detrimental interface between bone and the biomaterial. The presence of a biomaterial interposed within bone can interfere with normal bone remodeling processes and can ultimately result in bone resorption or stress fractures (Spector 1991). In addition, with scaffolds or carriers constructed from synthetic degradable polymers, such as poly(I-hydroxyesters), a relatively large volume of material, resulting in lower porosity, is required to produce a structure with sufficient strength. Consequently, there is less space available for bone formation and significantly greater quantities of degradation products. These degradation products can interfere with bone formation and can also result in bone resorption (Böstman 1992).

Many of these problems may be circumvented through the use of carriers such as collagen sponges which do not appear to significantly interfere with bone formation or remodeling even during the degradation phase of the material. However, collagen sponges, especially those with suitable degradation time frames, are generally not able to withstand the above-listed in vivo stresses and consequently are unable to maintain the size and shape of the filled space. As a result, the newly created bone assumes an ill-defined geometry which is not the same as the original shape of the sponge and which is often not of adequate or optimal functional or therapeutic benefit. Such an outcome is reported by Oppermann et al. (U.S. Pat. No. 5,354,557) who describes the use of a collagen sponge combined with osteogenic proteins for bone regeneration. Wolfe and Cook (1994) have also recognized the difficulty of controlling the geometry of bone formed using osteogenic proteins and state that the osteoinductive effect of the protein can be difficult to confine to a limited anatomic area, especially using semi-solid carrier vehicles. This same phenomenon can be seen with degradable synthetic polymer structures that, although they can be designed with appropriate mechanical stresses at the time of implantation, gradually lose their ability to withstand in vivo stresses and collapse at some point during degradation.

Kuboki et al. (1995) used bioactive molecules in conjunction with a flat, space-filling, unwoven glass fibril membrane to study bone formation. In this case, the majority of the tissue formed was cartilage that was located within the microstructure of the membrane. The desired bone tissue was therefore not formed and the cartilage tissue generated was associated with a non-degradable material that is likely to adversely influence the desirable properties of the natural tissue. Chu et al. (U.S. Pat. No. 5,219,576) describe a space filling collagen matrix with a thickness of 1–20 mm and a pore size of at least 30 Tm in diameter. The matrix is intended for use in skin/dermal wound healing and tissue regeneration and can be used in conjunction with bioactive molecules. The teachings of Chu et al. do not address the necessity of controlling the configuration of the tissue generated by the articles and methods of the invention. An improvement of these tissue regeneration methods is found in the field of guided tissue regeneration. Guided tissue regeneration is a therapeutic approach aimed at regenerating periodontal tissue and bone, particularly of the jaw. It is based on the concept of selective tissue exclusion and attempts to optimize the natural regenerative potential of the patient=s tissues. Exclusion of undesirable fibrous tissue from the regenerative space is achieved through the use of a membrane that acts as a passive physical barrier which is substantially impermeable to cells and tissues. In addition, the membrane maintains the regenerative space until such time as the tissue is regenerated. This technology has done much to advance the field of alveolar bone and periodontal tissue regenerative therapies, however, the widespread application of this technology has not been fully realized due to issues of predictability in the most clinically challenging situations.

Scantlebury et al. (U.S. Pat. No. 5,032,445) described the potential for a combination of tissue excluding guided tissue regeneration membranes and bioactive molecules. This concept was reiterated by Golgolewski (U.S. Pat. No. 5,676,699 and EP 0 475 077) who described a degradable, microporous bone regeneration membrane which may be used in conjunction with various bioactive molecules. The membrane was again used as a tissue separator which promotes and protects osseous regeneration. According to Golgolewski, the essential function of the micropores is that they are permeable for nutritional fluids. This statement is consistent with the most preferred pore diameter range of 0.1 to 5.0 Tm. Similar concepts have been reported by Sottosanti (U.S. Pat. No. 5,569,308), Dunn et al. (U.S. Pat. No. 5,077,049), Jemberg (U.S. Pat. Nos. 5,059,123 and 5,197,882) and Hehli (U.S. Pat. No. 5,383,931). Saffraran (U.S. Pat. No. 5,446, 262) for example, describes a two layered, tissue excluding membrane for the directional delivery of bioactive molecules for tissue repair.

The combination of bioactive molecules with guided tissue regeneration membranes has also been studied in small, experimental defects in rabbit long bones by Zellin and Linde (1997). In this model the combination of a bioactive molecule with a cell and tissue excluding membrane was successful in regenerating the bone defect. However, studies by Cochran et al. (1997) show that bone formation in the mandible is impeded by the use of a cell and tissue excluding membrane in combination with a bioactive molecule. In addition, studies by Hedner and Linde (1995) found that the combination of a cell and tissue excluding membrane and a bioactive molecule was less effective in stimulating bone healing in mandibular defects than the bioactive molecule alone. Predictable bone regeneration using a bioactive molecule and a membrane which excludes cells and tissue from the regenerative space has yet to be shown.

Khouri et al. (1991) describes the use of an osteogenic protein with a non-porous silicone rubber mold filled with a vascularized muscle flap and demineralized bone matrix. The muscle flap was transform into bone which matched the shape of the mold. One of the disadvantages of this technique is that it requires the use of living autogenous tissue, namely a muscle flap, which requires surgically injuring existing living tissue. In addition, vascularized muscle tissue may not be available for transplantation in specific areas, such as the oral cavity, especially without significantly affecting other functions of the patient.

Boyne (1996) used rhBMP-2 in conjunction with titanium orthopaedic plate mesh (TiMesh) to regenerate bone in a monkey mandible model. This mesh has a hole size of 2.2 mm and was used only as a mechanical support to stabilize the bone ends. The mesh device used does not define the configuration of a space having the size and shape desired for the bone to be generated. Some tissue sections from Boyne show extensive bone formation beyond the boundary of the mesh.

The use of membranes which are not tissue excluding has been studied by Pineda et al. (1996) for long bone regeneration. This study showed that the principles and mechanisms of guided bone regeneration do not operate when membranes are utilized with larger pore sizes that do not result in cell and tissue exclusion. Consequently, significantly less bone regeneration results with large pore size membranes which do not exclude cells and tissue. Haris (U.S. Pat. No. 4,787,906) describes a similar system for alveolar ridge augmentation which utilizes inert particles contained within a porous tube designed to allow tissue through growth. The teachings of Haris specify fibrovascular invasion into the tube, but this invention does not teach the use of bone inductive agents.

Tepic (U.S. Pat. No. 5,211,664 and EP 0 551 611) teaches the use of a structure for long bone regeneration which comprises two concentric, parallel, tubular shells connected to each other by struts. One or both of the shells may be provided with interconnected micropores and therefore, according to the author, diffusion alone is sufficient to maintain grafted metabolism in the critical phase before revascularization takes place. The author further states that the shells of the concentric tubular structure may also have larger openings in the range of 0.1 to 2.0 mm which allow for vascular ingrowth from surrounding tissue. However, the author espouses adherence to the above-summarized teachings of guided tissue regeneration in which a membrane or sheet structure is used to substantially exclude soft tissue and soft tissue ingrowth from the space created by the membrane. Indeed, the most preferred embodiments are consistent with the teachings of guided tissue regeneration and stipulate the use of a concentric membrane structure with pore diameters in the range 0.1 to 5.0 Tm. The structure is also intended to serve as a container for bone grafts or various bioactive agents.

The use of macroporous membranes in conjunction with autograft bone for long bone regeneration has been studied by Gerber and Golgolewski (1996) and later by Gugala and Golgolewski (1997). In these studies, a long bone defect was filled with autograft bone and covered with a macroporous membrane. Although these studies showed that it is possible to regenerate bone in this manner, this approach also resulted in massive resorption of the graft. In order to ameliorate the undesirable resorption outcome, two concentric macroporous membranes were required; one inserted into the medullary canal and the other placed on the periphery of the defect with the annular space filled with autograft bone. It is clear that long bone defects do not heal appropriately in the long term using a combination of autograft bone and a single macroporous membrane. Furthermore, in order to appropriately utilize the regenerative potential of autograft bone in long bone defects a highly specific device design involving concentric macroporous membranes is required. An additional drawback of this methodology is that it requires the use of autologous tissue in quantities at least sufficient to fill the defect.

Lemperle et al. (1996) has studied the use of a titanium mesh as a containment system for autograft bone. These studies have shown that with this system, it is possible to regenerate only as much bone over a 4 month period as is regenerated using a titanium mesh placed over an empty defect. Holmes (1997) has also postulated the use of a resorbable macroporous sheet as a containment system for bone grafts and Patyk (DE 91 15 341) describes a similar system for bone substitute materials. However, as the studies of Gugala and Golgolewski show, the use of a single macroporous sheet in conjunction with autograft bone does not result in a satisfactory long term healing response at least for long bone applications. In addition, this approach also requires the use of autologous tissue to fill the defect.

Teixeira and Urist (1997) describe the use of macroporous membrane, with pores 0.5 mm in diameter, in conjunction with a mixture of bovine derived bone morphogenetic protein and associated non-collagenous bone matrix protein for long bone regeneration.

Lemperle (WO 98/07384) describes a macroporous membrane structure for tissue reconstruction. The reference teaches that regeneration of bone and other tissues may be achieved solely through the use of a macroporous membrane which prevents prolapse of the surrounding soft tissue and allows ingrowth of blood vessels and connective tissue. However, as the long bone regeneration studies of Pineda et al. (1996) show, the principles and mechanisms of guided bone regeneration do not operate when membranes are utilized with larger pore sizes that do not result in cell and tissue exclusion. Significantly less bone regeneration results with large pore size membranes which do not exclude cells and tissue.

Although the Lemperle reference focuses on the merits of the macroporous membrane structure in tissue and bone regeneration, mention is also made of the possibility of impregnating the membrane with substances for promoting the regeneration of different tissues such as bone and blood vessels. Although delivery of a bioactive substance from a membrane may appear to be an attractive proposition, there are significant biological and technical shortcomings of this approach. It is technically difficult to achieve delivery of therapeutically effective quantities of an appropriate bioactive molecule from a membrane. For example, it is not always possible to load sufficient quantities of a bioactive agent onto a membrane by relying on simple adsorption of the molecules onto the membrane surface, especially if the membrane is constructed from a hydrophobic material. Materials which are hydrophobic in nature are most often used to construct membranes since they have superior mechanical properties over hydrophilic materials such as collagen.

Even if sufficient loading of the membrane can be achieved, the next obstacle is providing an appropriate delivery profile. In general, bioactive agents must be made biologically available to the host for a of several days in order to stimulate significant bone formation. This is why other tissue generation approaches use a controlled or sustained release device to deliver the bioactive agent over a sufficient period of time (Bessho, 1996). It is not generally possible to achieve such a sustained release profile via simple adsorption and desorption of the bioactive molecule from a membrane, however. An adsorption-desorption mechanism results in a so-called burst effect in which most of the bioactive substance is released in the first one or two days after implantation.

In addition to the technical difficulties involved in achieving appropriate delivery of a bioactive agent from a membrane, it has not been shown that delivery of a bioactive molecule from a macroporous and tissue penetrable membrane surrounding the periphery of a bone defect is efficacious in regenerating bone. The presence of macropores in the membrane allows diffusion of the bioactive molecule both inward toward the center of the defect and outward toward the surrounding soft tissue. This has two distinct disadvantages. First, the presence of the bioactive molecule in high concentrations near the outer surface of the membrane would be likely to cause bone to form on the outside of the membrane thus resulting in a lack of control of the regenerated bone geometry. Second, diffusion of the bioactive molecule inward toward the center of the defect would result in an adverse concentration gradient for the migration of cells, such as mesenchymal stem cells, from the tissue surrounding the defect. The migration of cells in response to a local concentration gradient is known as chemotaxis and is normally associated with cellular migration toward the highest concentration of a chemotactic substance. In the case of membrane delivered bioactive molecules, the lowest concentration would be at the center of the defect and the highest concentration at the surface of the membrane. Mesenchymal stem cells would therefore be expected to migrate toward the membrane and not toward the center of the defect where they are needed to facilitate bone regeneration.

In summary, studies have been performed which utilize non-macroporous, tissue excluding membranes in conjunction with bioactive agents (Cochran et al. (1997) and Hedner and Linde (1995)). In each case, a bioactive agent delivered in an appropriate manner from a carrier material filling the space under a tissue excluding membrane did not achieve the desired bone regeneration result. In addition, desired bone regeneration is not attained when a macroporous membrane, which does not result in cell and tissue exclusion, is used alone (Pineda et al. (1996)). Although impregnating a macroporous membrane with bioactive molecules (Lemperle (WO 98/07384)) may result in bone formation, the regenerated tissue is unlikely to conform to the desired configuration defined by the geometry of the membrane.

Currently there is a need to predictably generate bone and periodontal tissue within the body of a mammal and to control the configuration of the tissue generated without using autologous tissue. It would be highly desirable, therefore, to have a combination of a macroporous membrane with TGF-Beta protein delivered from the space established by a device which results in predictable regeneration of bone or periodontal tissue, having a controlled configuration.

CITED REFERENCES

| U.S. PATENT DOCUMENTS | | |
|---|---|---|
| 5,683,459 | 11/1997 | Brekke |
| 5,219,576 | 06/1993 | Chu |
| 5,354,557 | 10/1994 | Oppermann |
| 5,032,445 | 07/1991 | Scantlebury |
| 5,676,699 | 10/1997 | Golgolewski |
| 5,569,308 | 10/1996 | Sottosanti |
| 5,077,049 | 12/1991 | Dunn |
| 5,059,123 | 10/1991 | Jernberg |
| 5,197,882 | 03/1993 | Jernberg |
| 5,383,931 | 01/1995 | Hehli |
| 5,466,262 | 11/1995 | Saffran |
| 4,787,906 | 11/1988 | Haris |
| 5,211,664 | 05/1993 | Tepic |

-continued

FOREIGN PATENT DOCUMENTS

| WO98/07384 | 02/1998 | Lemperle | PCT Int = 1 Appl. |
| G9115341.7 | 04/1992 | Patyk | Germany. |
| 0475077B1 | 03/1992 | Golgolewski | European pat. Off. |
| 0551611B1 | 07/1993 | Tepic | European pat. Off. |

Other Publications

Bessho, Ectopic Osteoinductive Difference Between Purified Bovine and Recombinant Human Bone Morphogenetic Protein. In bone Morphogenetic Proteins: Biology, Biochemistry and Reconstructive Surgery, ed. Lindholm T. S., Academic Press, Austin Tex., 1996.

Spector, Ceramic Materials and Bone Regeneration. In Proceedings of Portland Bone Symposium, eds. Seyfer A. E. and Hollinger J., Portland Oreg. 1991.

Böstman, Intense Granulomatous Inflammatory Lesions Associated with absorbable Internal fixation Devices made of Polyglycolide in Ankle fractures. Clinical Orthopaedics, 278:193, (1992).

Cochran et al., Radiographic Analysis of Regenerated Bone Around Endosseous Implants in the Canine Using Recombinant Human Bone Morphogenetic Protein-2, The International Journal of Oral & Maxillofacial Implants, Vol. 12, Number 6, (1997).

Hedner et al., Efficacy of Bone Morphogenetic Protein (BMP) with osteopromotive membranes—an experimental study in rat mandibular defects, Eurpean Journal of Oral Sciences, Vol. 103: 236–241, (1995).

Wolfe et al., Use of Osteoinductive Implants in the Treatment of Bone Defects, Medical Progress through Technology, 20: 155–168, (1994).

Kuboki et al., Two Distinctive BMP-Carriers Induce Zonal Chondrogenesis and Membrane Ossification, Respectively: Geometric Factors of Matices for Cell-Differentiation, Connective Tissue Research, Vol. 32, Nos. 1–4, pp. 219–226, (1995).

Zellin et al., Treatment of Segmental Defects in Long Bones Using Osteopromotive Membranes and Recombinant Human Bone Morphogenetic Protein-2, Scand. J. Plast. Reconstr. Hand Surg., 31: 97–104, (1997).

Khouri et al., Tissue Transformation Into Bone In Vivo, Journal of the American Medical Associate, Vol. 266, No. 14: 1953–1955, (1991).

Boyne et al., Animal Studies of the Application of rhBMP-2 in Maxillofacial Reconstruction, Bone, Vol. 19, No.1, 83S–92S, (1996).

Pineda et al., Bone Regeneration with Resorbable Polymeric Membranes. III. Effect of Poly(L-lactide) Membrane Pore Size on the Bone Healing Process in Large Defects, Journal of Biomedical Materials Research, Vol. 31, 385–394, (1996).

Gerber et al., Treatment of Large Diaphyseal Bone Defects Using Polylactide Membrane in Combination with Autogeneic Cancellous Bone, Fifth World Biomaterials Congress, Toronto, Canada, (1996).

Gugala et al., Regeneration of Bone in Large Segmental Diaphyseal Defects using Tube-in-Tube Resorbable Polymeric Implants, $23^{rd}$ Annual meeting of the Society for Biomaterials, New Orleans, La., (1997).

Lemperle et al., Comparison of Protected Bone Regeneration, Osteoconduction with Coralline Hydroxyapatite Implants, and Cancellous Bone Autografts in Large Cranial and Mandibular Defects in Dogs, Surgical Forum, 47: 723–27, (1996).

Holmes, A Macroporous Protective Sheet for Bone Regeneration and Implant Containment, IBC=s First Annual International Conference on Orthopaedic Biomaterials, San Diego, Calif., (1997)

Teixeira et al., Bone Morphogenetic Protein induced repair of Compartmentalized Segmental Diaphyseal Defects, Archives of Orthopedic Trauma Surgery, 117: 27–34, (1997).

Figure 1A:
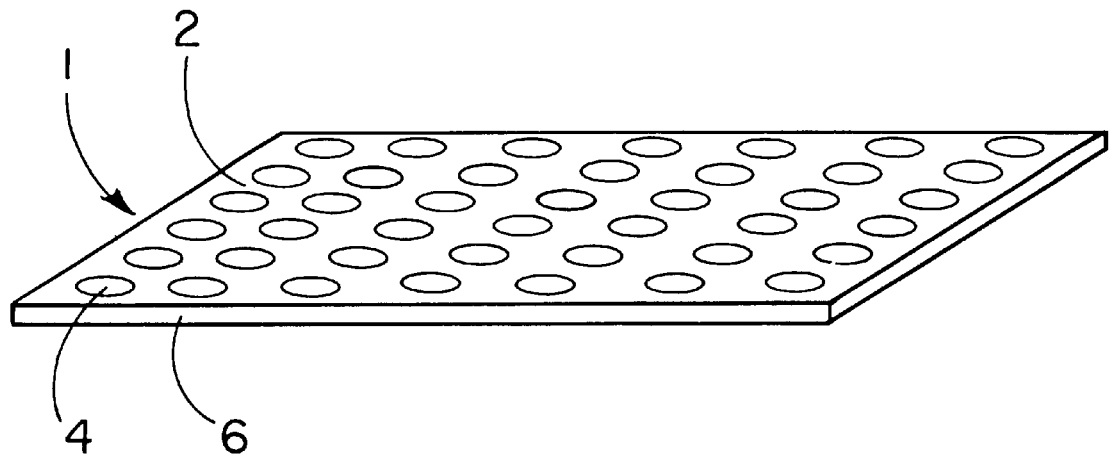
FIG. 1A illustrates a component of the present invention (1) having a plurality of holes (4) in material (2) having a thickness (6).
Figure 1B:
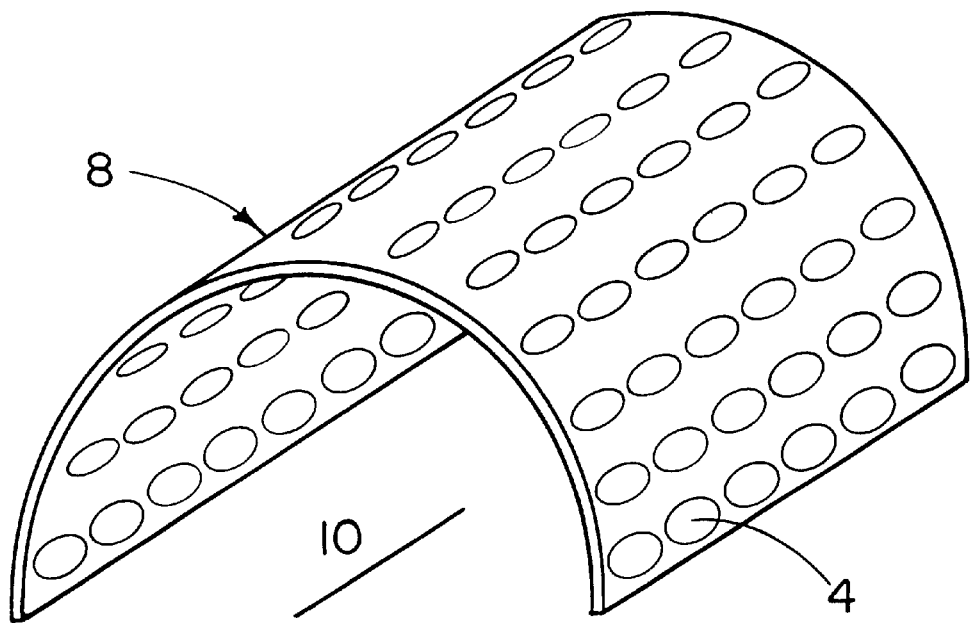
FIG. 1B illustrates a component of the present invention (8) of FIG. 1A that has been shaped to form a delimited space (10).
Figure 2A:
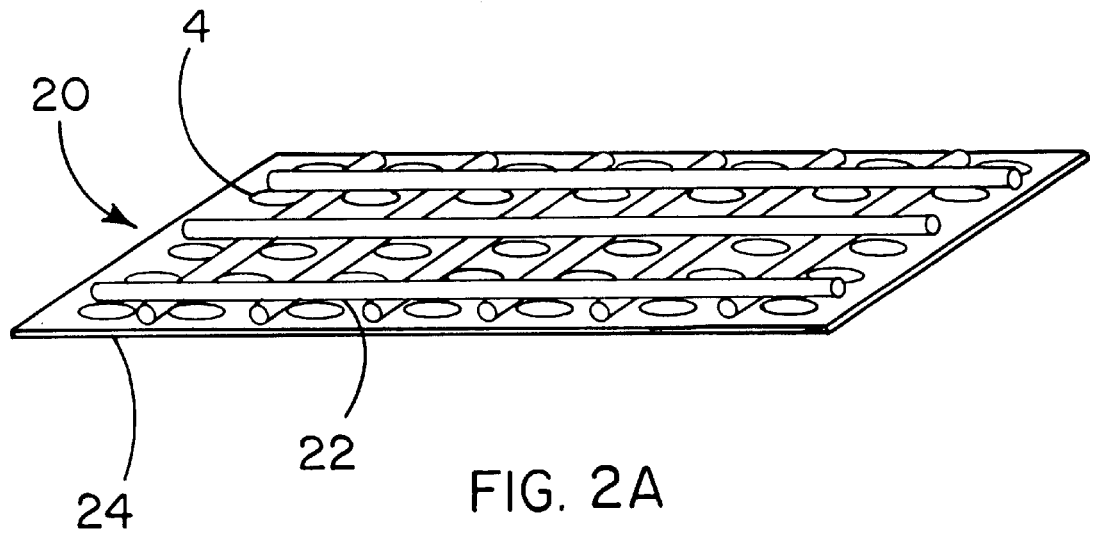
FIG. 2A illustrates a component of the present invention (20) having a plurality of holes (4) in the material (24) having reinforcement members (22) therein.
Figure 2B:
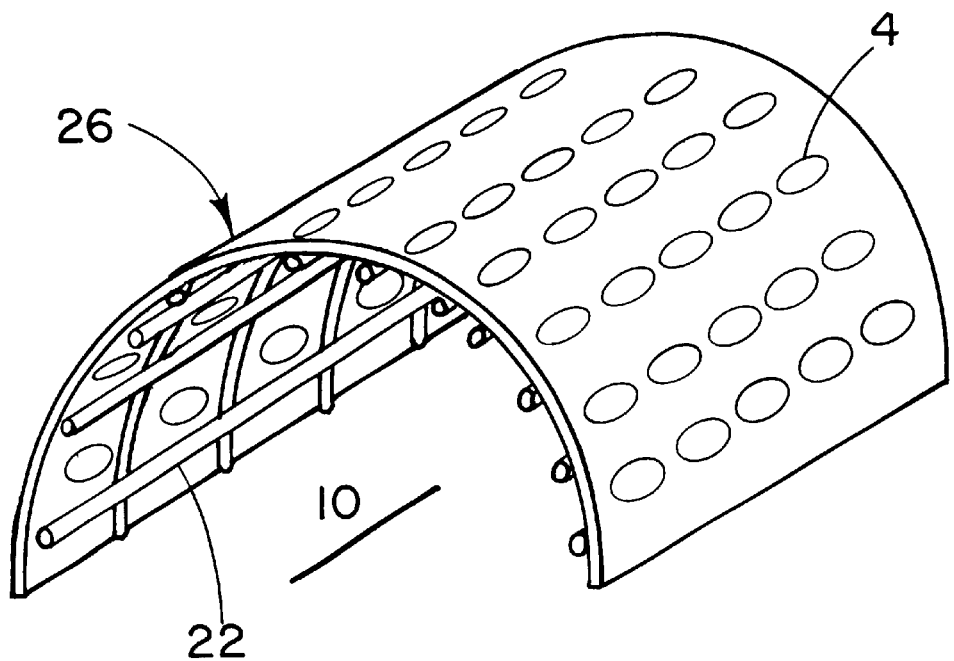
FIG. 2B illustrates a component of the present invention (26) of FIG. 2A that has been shaped to form a delimited space (10).
Figure 3A:
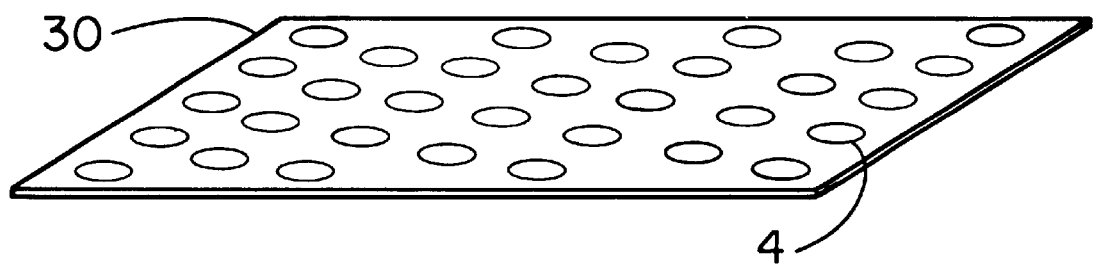
FIG. 3A illustrates a component of the present invention (30) having a plurality of holes (4) in a pattern.
Figure 3B:
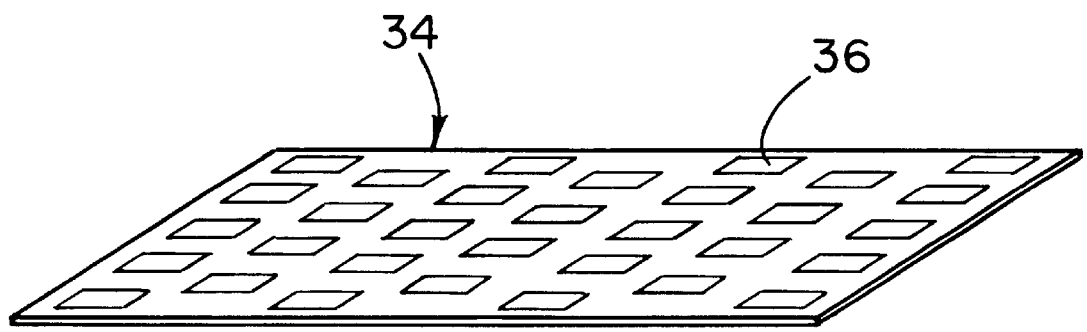
FIG. 3B illustrates a component of the present invention (34) having a plurality of holes (36) in a pattern.
Figure 3C:
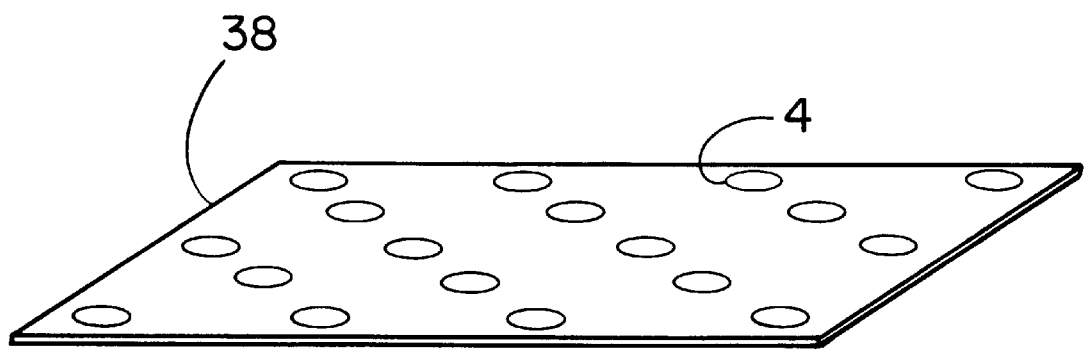
FIG. 3C illustrates a component of the present invention (38) having a plurality of holes (4) in a pattern.
Figure 4:
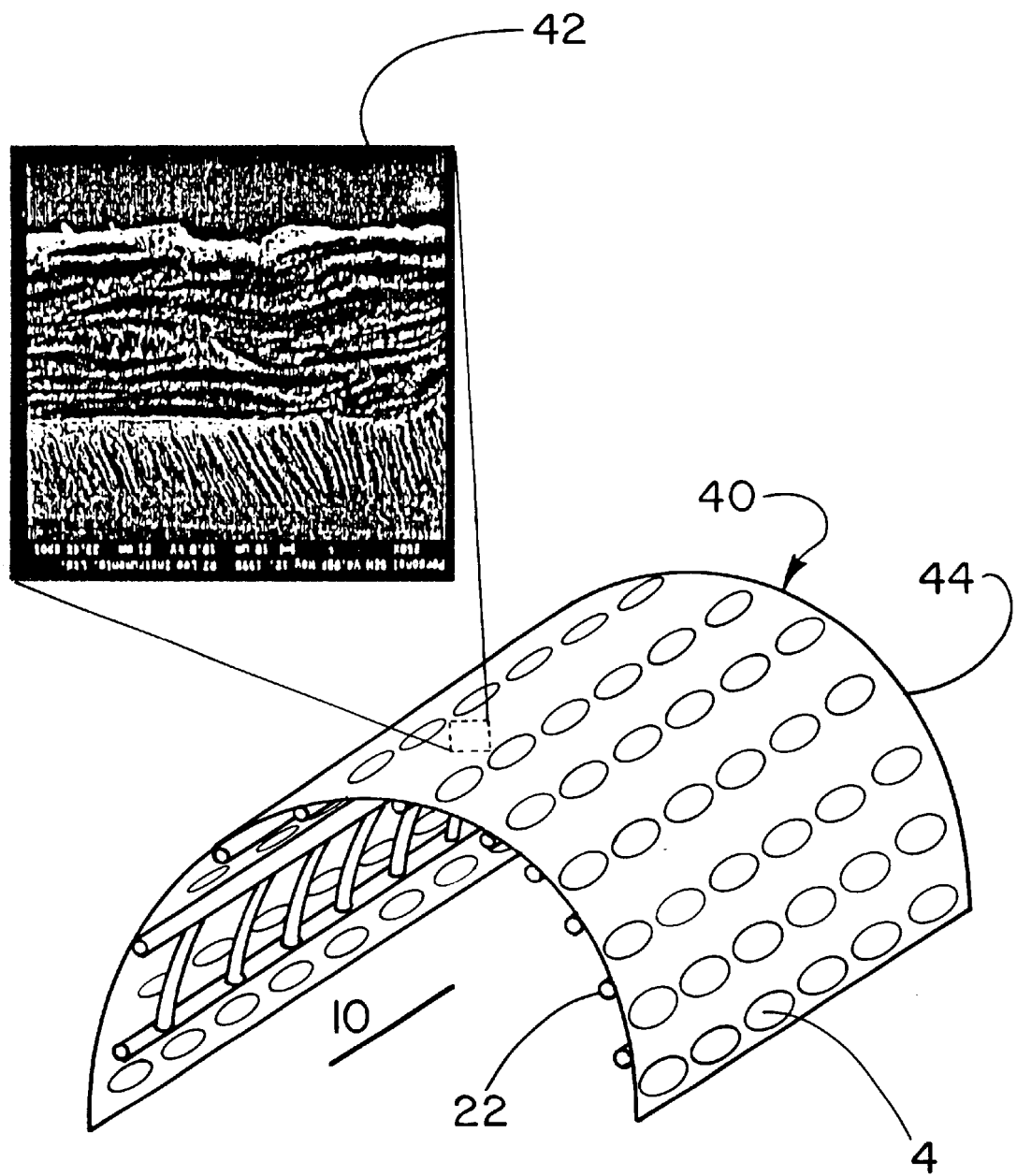
FIG. 4 illustrates a component of the present invention (40) having a plurality of holes (4) in material (44), reinforcement members (22) and delimited space (10). The Figure also shows an exploded view (42) of the microstructure of material (44).
Figure 5A:
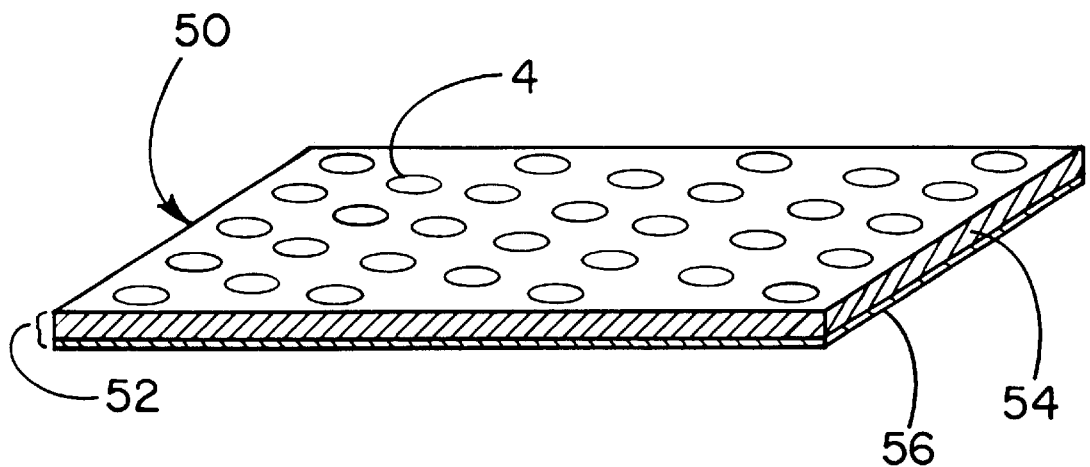
FIG. 5A illustrates a component of the present invention (50) having a plurality of holes (4) in material (52), wherein material (52) is a laminate of material (54) and material (56).
Figure 5B:
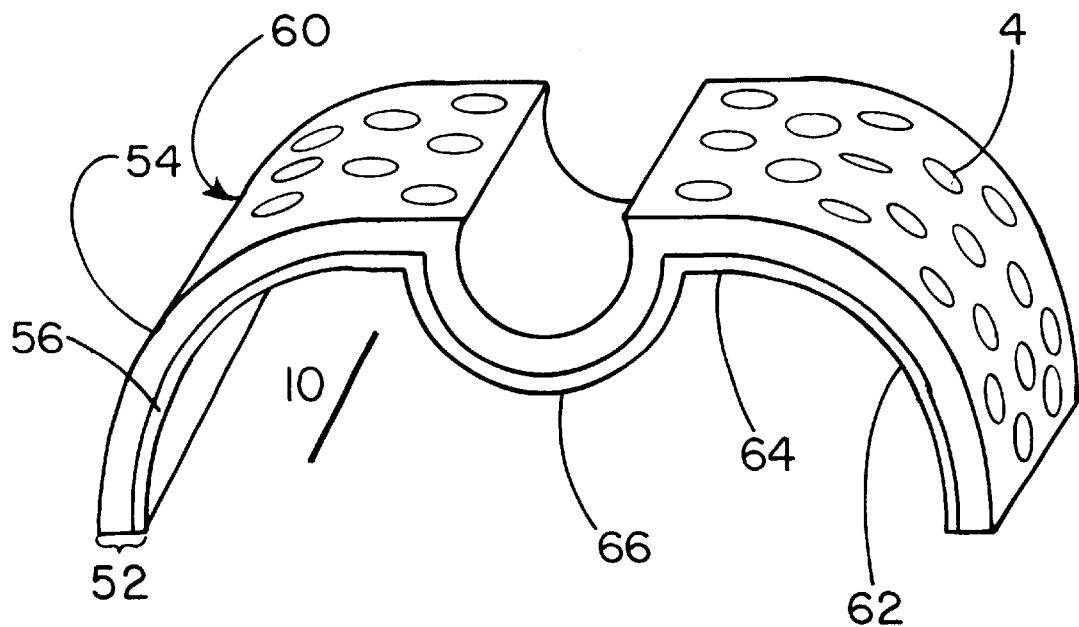
FIG. 5B illustrates a component of the present invention (60) having a plurality of holes (4) in material (52), wherein material (52) is a laminate of material (54) and material (56), and wherein the material (52) has a concave shape (62), a convex shape (66), and an irregular shape (64).
Figure 6:
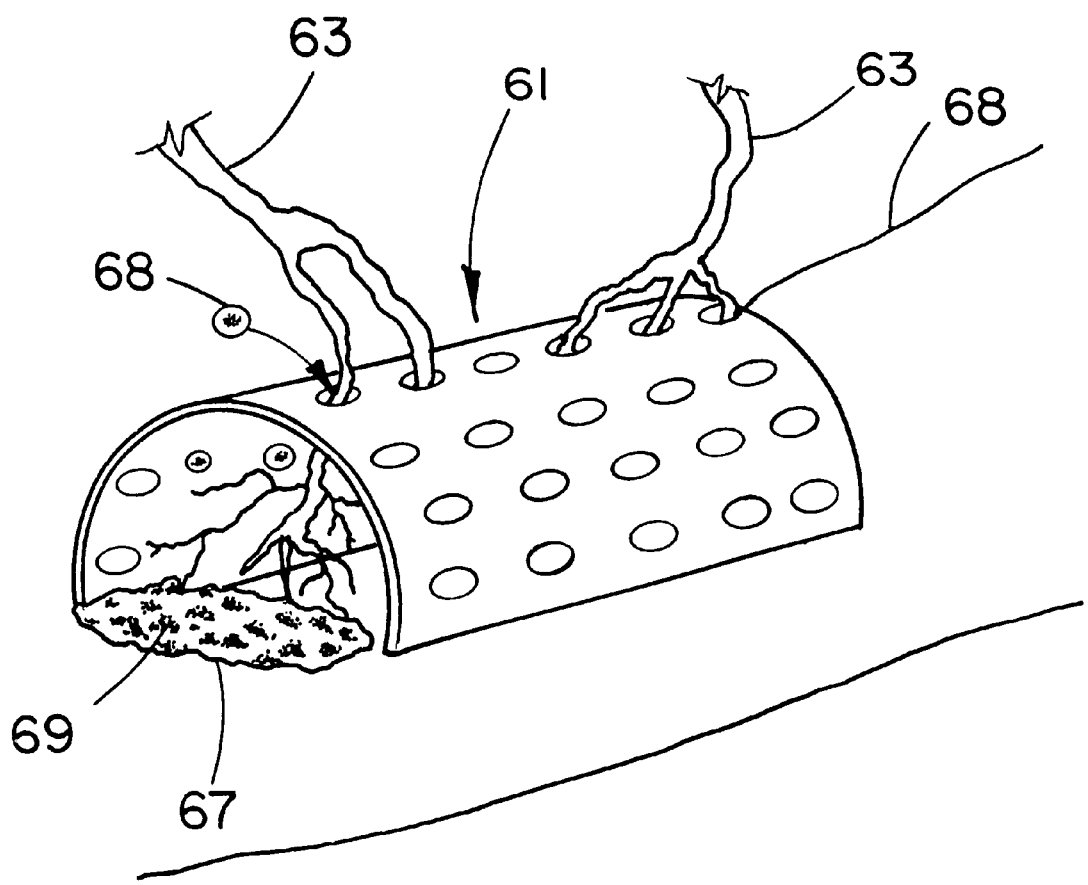
FIG. 6 illustrates an aspect of the present invention (61) placed in tissue of a host (68) having host blood vessels (63) growing through through and through holes (4) of the invention. Cells (68) are also illustrated passing through holes (4). A carrier matrix (67) having a TGF-Beta protein (69) is also shown.
Figure 7:
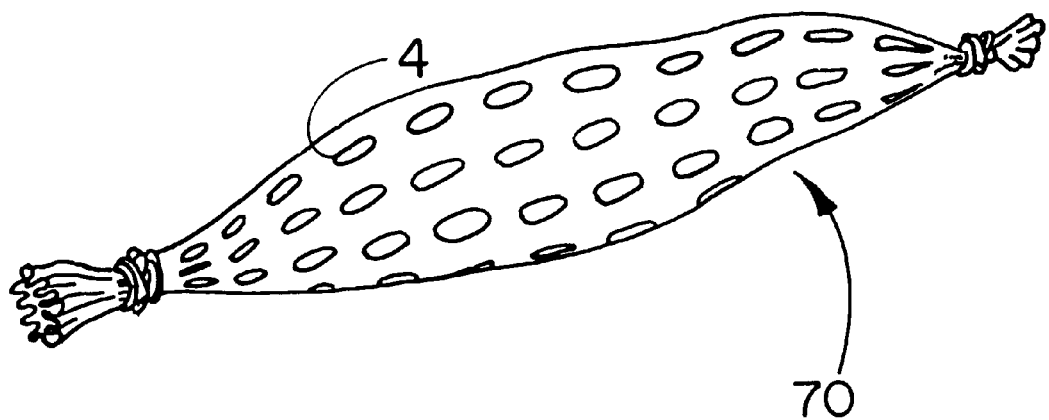
FIG. 7 illustrates an aspect of the present invention (70) in a tubular form with ends tied.

growing through holes (4) of the invention. A carrier matrix (67) having a TGF-Beta protein (69) is also shown placed within the delimited space (10) which is defined solely by a tubular TP device (12) having a thickness (6).

Figure 11:
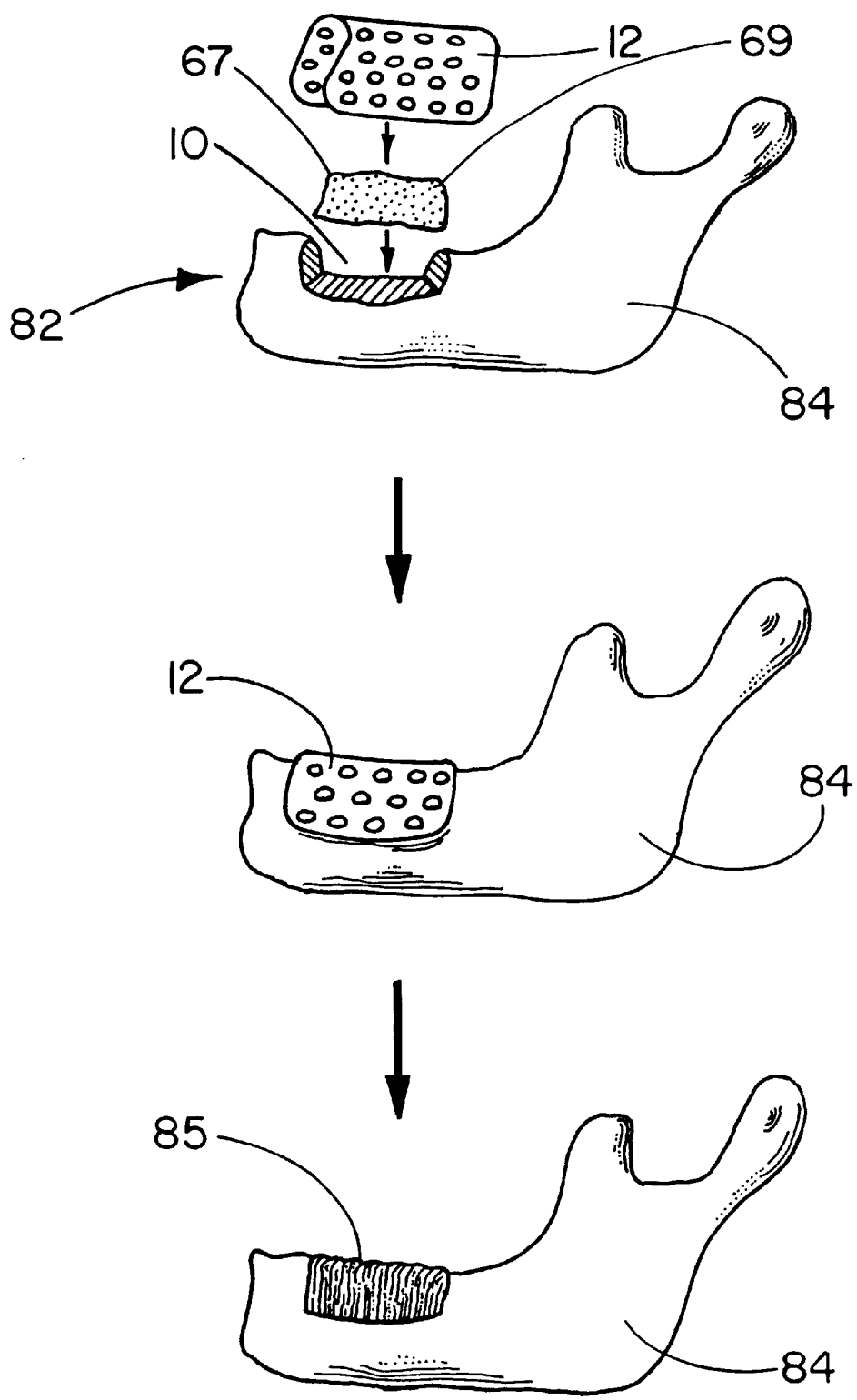

FIG. 11 illustrates an aspect of the present invention (82) wherein a TP device (12) is placed in tissue of a host to effect repair of a bone defect in the mandible (84). A carrier matrix (67) having a TGF-Beta protein (69) is also shown placed within the space (10) being defined by the TP device (12) and mandible (84). The generated bone (85) has the essentially the same configuration as the space defined by the TP device (12) and mandible (84).

Figure 12:
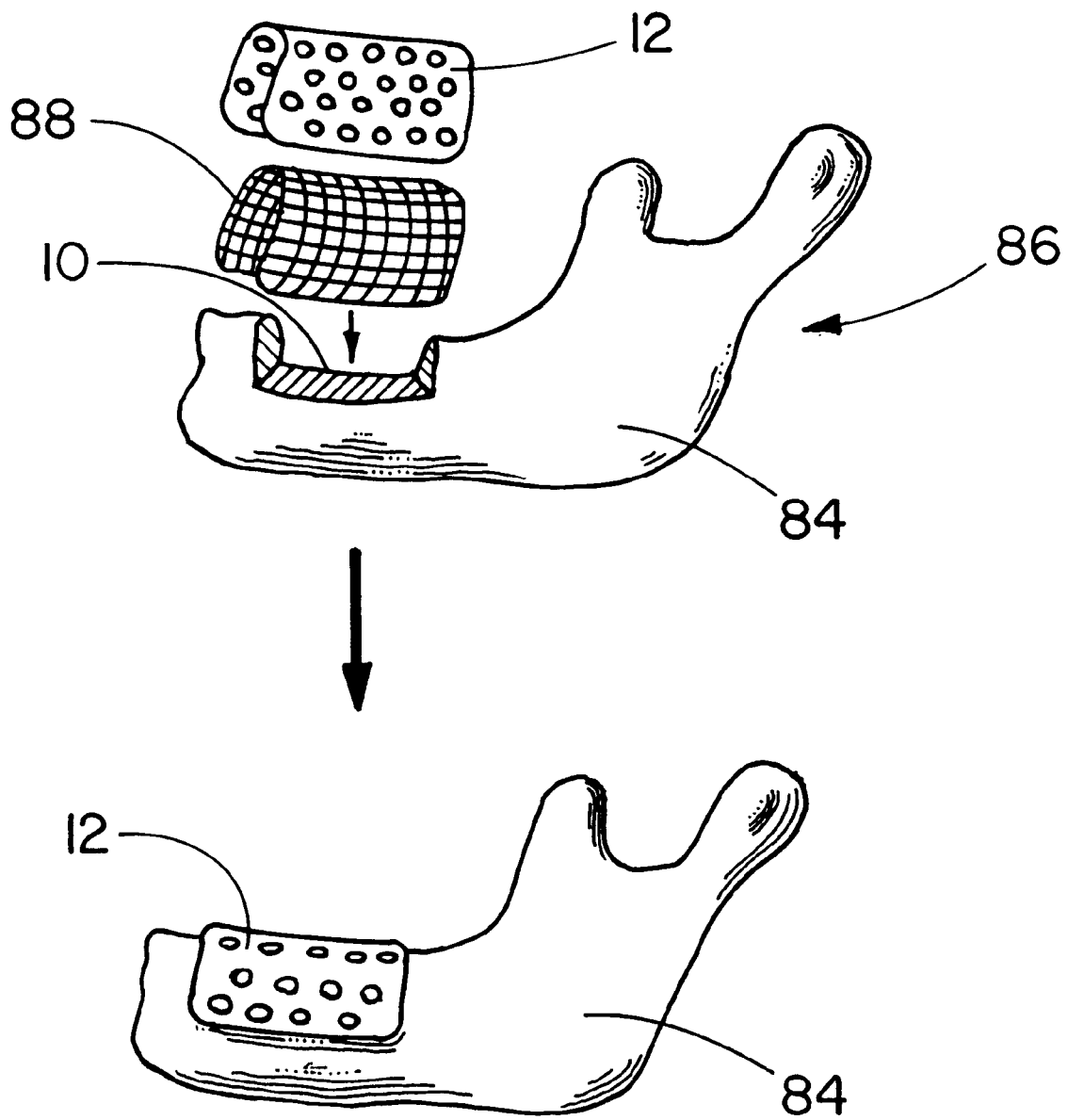

FIG. 12 illustrates an aspect of the present invention (86) wherein a cage (88) of open structure is placed under a TP device (12) in tissue of a host to effect repair of a bone defect in the mandible (84). The cage (88) aids in preventing collapse of the TP device (12) into the space (10) defined by the TP device (12) and mandible (84).

Figure 13A:
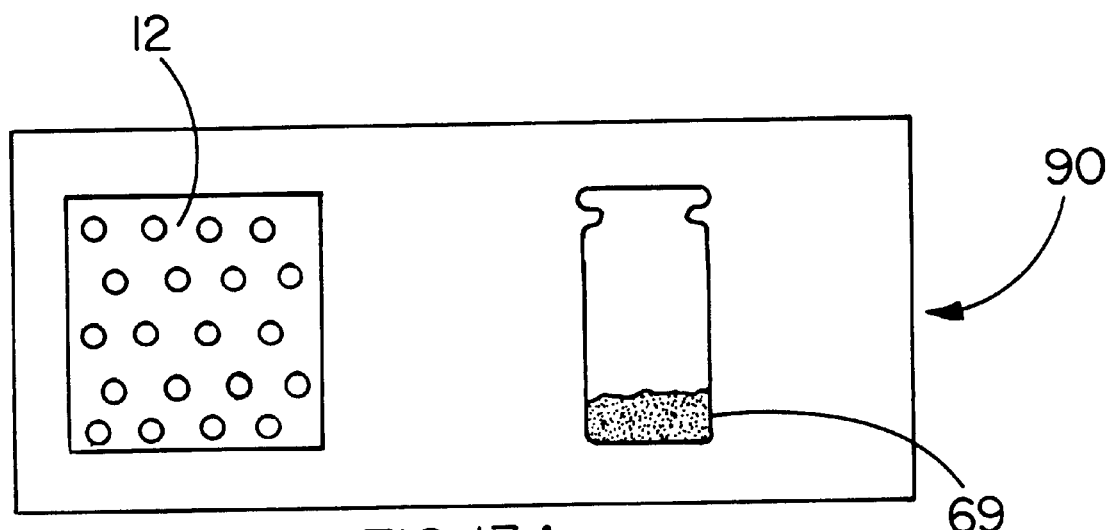

FIG. 13A illustrates an aspect of the present invention (90) wherein a kit comprises a configurable TP device (12) and a TGF-Beta protein (69).

Figure 13B:
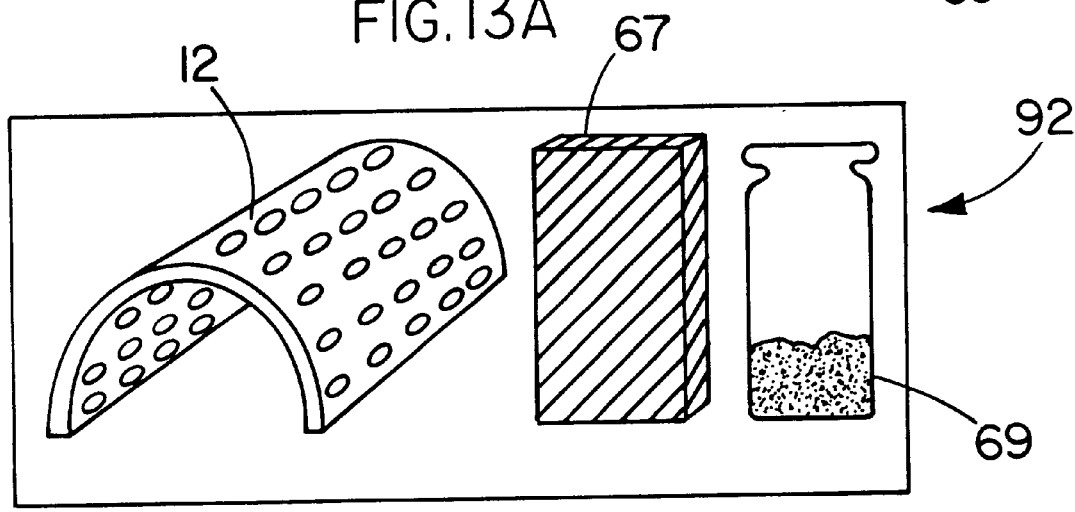

FIG. 13B illustrates an aspect of the present invention (92) wherein a kit comprises a configured TP device (12), a carrier matrix (67) and a TGF-Beta protein (69).

Figure 13C:
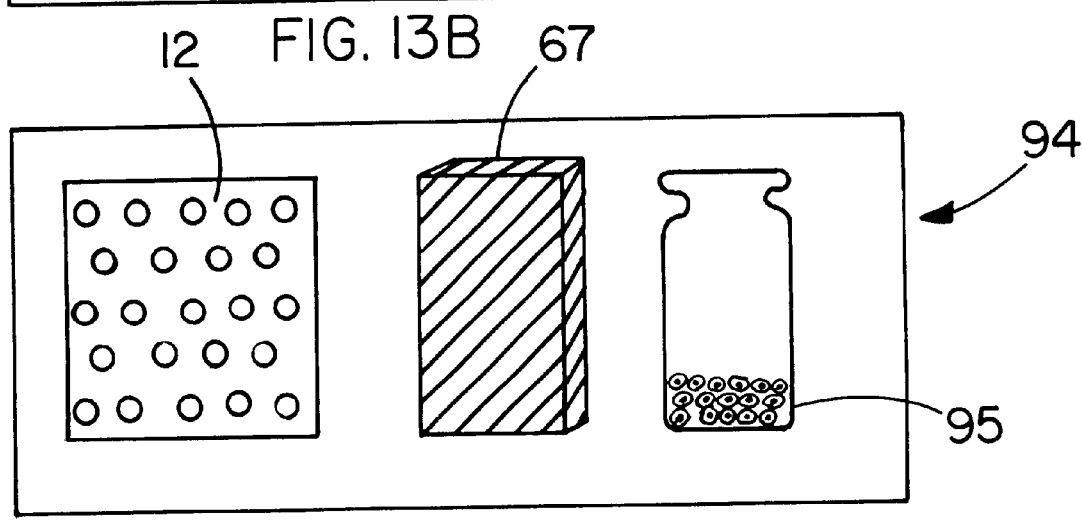

FIG. 13C illustrates an aspect of the present invention (94) wherein a kit comprises a configurable TP device (12), a carrier matrix (67) and cryopreserved cells (95).

Figure 14:
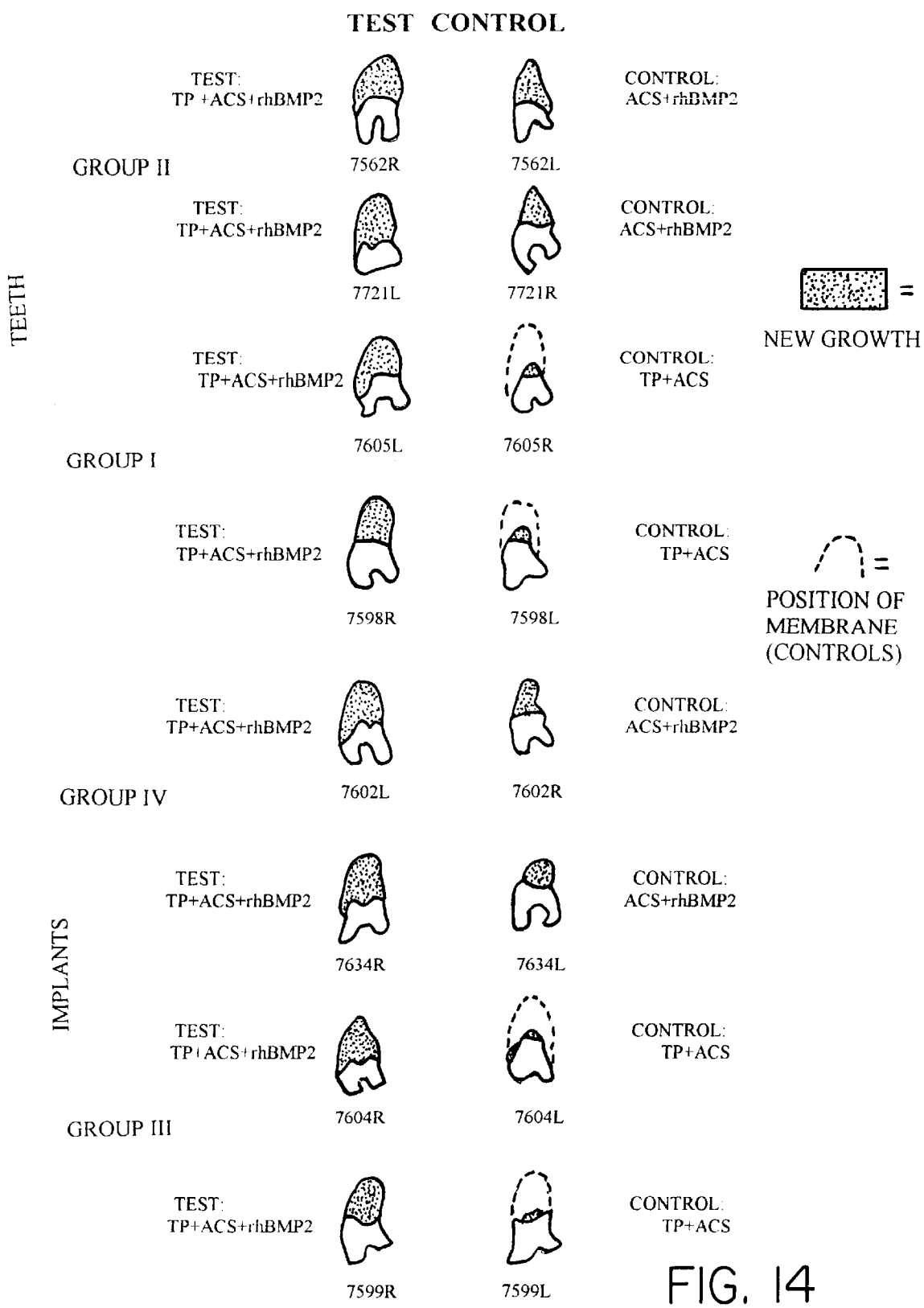

FIG. 14 illustrates schematic representations of cross-sectional CT scans between teeth or dental implants for the test and control sites described in examples 3, 4, 5, and 6.

Figure 15A:
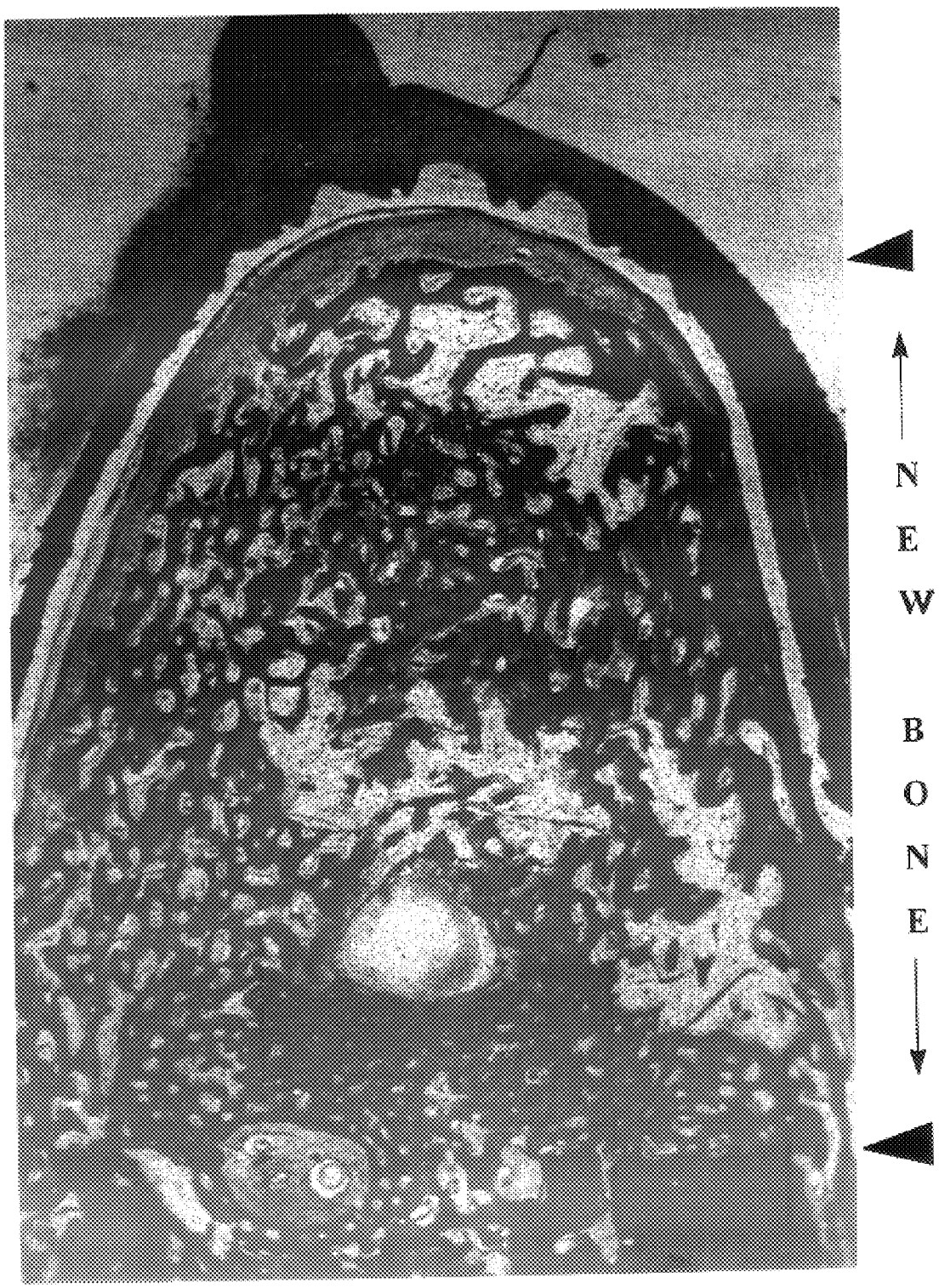
Figure 15B:

FIG. 15 illustrates histological cross-sections from peri-implant test sites receiving TP+ACS+rhBMP-2 (FIG. 15A) and control sites receiving ACS+rhBMP-2 (FIG. 15B).

SUMMARY OF INVENTION

There are numerous medical situations involving deficiencies of living bone or periodontal tissue and where increase of living bone or periodontal tissue mass is desired.

This invention describes a method of generating living bone or periodontal tissue having desired configuration in a mammal (said mammal including humans), said method comprising: providing a tissue penetrable device (TP device) comprising portions having a plurality of holes therethrough, wherein said holes permit cells and vascular structures to grow through said tissue penetrable device, said tissue penetrable device having mechanical properties that allow the device to be configured into a desired form and retained substantially in said desired form; establishing a space with said tissue penetrable device in a mammal in such a way that a boundary is at least partially formed by said tissue penetrable device between said space and anatomical structures of said mammal surrounding said space, wherein said space has essentially the same configuration as bone or periodontal tissue to be generated therein; placing at least one TGF-Beta protein in said space; allowing cells and blood vessels from said mammal to traverse said tissue penetrable device through said holes into said space; and generating bone or periodontal tissue in said space.

Controlled configuration of the generated bone or periodontal tissue is achieved when the living bone or periodontal tissue generated has essentially the same configuration as the space established upon implantation of the TP device.

The TP device is comprised of a flattened member constructed essentially of biocompatible materials, that is configured into a desired configuration. When implanted, the TP device provides a porous permeable boundary between the living tissues of the mammal and the established space. The TP device therefore takes the form of a porous permeable shell. The TP device may delineate the entire boundary of the space, or the device may delineate only a portion of the space; the remainder of the boundary being delineated by tissues of the mammal. The configuration (size and shape) of the space established by implantation of the device is essentially equivalent to the configuration of living bone and periodontal tissue desired for functional and/or aesthetic treatment of the mammal. Preferably, generation of living bone or periodontal tissue does not occur substantially outside the space established by the TP device.

The TP device is provided with a plurality of pores that pass through the wall thickness of the device. The important feature of the pores is they allow blood vessels and cells originating from the living tissues peripheral to the space established by the device to grow completely through the wall thickness of the device such that they penetrate into the space established by the device. Preferably, the pores are constructed such that they pass directly through the wall of the device. The TP device of the present invention is provided with pores having a nominal size in the range of about 3 micrometers to about 3000 micrometers. Preferably the nominal size of the pores should be in the range of about 50 micrometers to about 1000 micrometers, and most preferably in the range of about 150 micrometers to about 500 micrometers.

Members of the TGF-Beta Superfamily of proteins (TGF-Beta Proteins) have numerous potential effects, most of which stimulate growth and development of cells and tissues. TGF-Beta proteins are placed within the space established, by implantation of the TP device, in order to stimulate cell differentiation, cell proliferation, cell migration, or the production of extracellular matrix substances such as collagen.

In many situations, a carrier substance, such as collagen or hyaluronic acid, is preferred for delivery of the TGF-Beta protein.

The present invention also describes a kit for generating living bone or periodontal tissue having desired configuration in a mammal, said kit comprising: a tissue penetrable device comprising portions having holes therethrough, wherein said holes permit cells and vascular structures to grow through said tissue penetrable device, said tissue penetrable device having mechanical properties that allow the device to be configured into a desired shape and retained substantially in said desired shape; and at least one TGF-Beta protein.

DETAILED DESCRIPTION OF INVENTION

There are numerous medical situations involving deficiencies of living bone or periodontal tissue and where increase of living tissue mass is desired.

This invention describes methods and components for generation of living bone or periodontal tissue within the body of a mammal (said mammal including humans) and controlling the configuration of the living tissue generated.

Generation here means the production, restoration or regeneration of living bone or periodontal tissue within the body of a mammal. Living bone tissue here refers to the level of biological organization representing the major components of bone including bone cells that are generally located within a matrix of mineralized collagen; blood vessels that provide nutrition for the bone cells; and may include fatty bone marrow and/or cells that give rise to components of the blood. Periodontal tissue refers to the functional association of alveolar bone, periodontal ligament, and tooth root cementum.

Generation of living bone and periodontal tissues with controlled configuration is achieved by surgically implanting a tissue penetrable (TP) device, the implantation of which establishes a space of desired configuration within the body of the mammal. Furthermore, the TP device is implanted in conjunction with one or more proteins from the Transforming Growth Factor-Beta (TGF-Beta) Superfamily of proteins that are placed within the space established by the device.

Controlled configuration of the generated bone or periodontal tissue is achieved when the living bone or periodontal tissue generated has essentially the same configuration as the space established upon implantation of the TP device.

The TP device is comprised of a flattened member constructed essentially of biocompatible materials, that is configured into a desired configuration. Configuring of the device may take place during construction of the device. Alternatively, the device may be configured after construction; for example during implantation. When implanted, the TP device provides a porous permeable boundary between the living tissues of the mammal and the established space. The TP device therefore takes the form of a porous shell and may delineate the entire boundary of the space, or alternatively, the device may delineate only a portion of the space; the remainder of the boundary being delineated by tissues of the mammal. The configuration (size and shape) of the space established by implantation of the device is essentially equivalent to the configuration of living bone and periodontal tissue desired for functional and/or aesthetic treatment of the mammal. Preferably, generation of living bone or periodontal tissue does not occur substantially outside the space established by the TP device.

The TP device is provided with a plurality of pores that pass through the wall thickness of the device. These pores may have varying characteristics such as shape or tortuosity. However, the important feature of the pores is they allow blood vessels and cells originating from the living tissues peripheral to the space established by the device to grow completely through the wall thickness of the device such that they penetrate into the space established by the device. Preferably, the pores are constructed such that they pass directly through the wall of the device.

The TP device pore structure is described here using nominal pore sizes. These nominal pore sizes are related to measurable parameters so that practical and accurate methods can be employed to define the scope of the invention.

The TP device of the present invention is provided with pores having a nominal size in the range of about 3 micrometers to about 3000 micrometers. Preferably the nominal size of the pores should be in the range of about 50 micrometers to about 1000 micrometers, and most preferably in the range of about 150 micrometers to about 500 micrometers. Smaller pores in the nominal size range of about 3 micrometers to 20 micrometers, as established by ethanol bubble point, may allow the ingrowth of small blood vessels sufficient to effect generation of living bone or periodontal tissue. However, it is thought that larger pores, in the range of about 20 micrometers to about 3000 micrometers will encourage the through-growth of larger blood vessels that will in turn be able to support more rapid generation of bone or periodontal tissue within the established space. Additionally, it is thought that very large pores, with a nominal pore size greater than about 3000 micrometers will, in some cases, allow soft tissues peripheral to the TP device to protrude into the established space, thus decreasing the ability to control the configuration of bone or periodontal tissue generated within the space.

The pores of the TP device may all have nominal sizes in the above-described ranges, or only a portion of the pores may have nominal sizes in the range of about 3 to 3000 micrometers. The important feature is that the TP device is provided with a plurality of pores with nominal sizes in the above-described ranges. When only a portion of the pores have nominal sizes in the above-described ranges, it is preferable that the remaining portion of the pores have nominal sizes of less than about 3 micrometers.

Numerous methodologies exist for characterization of pore size. However, there is no one practical methodology known to the inventors which are both accurate and practical over the entire nominal pore size range of the present invention. The pore size range of the present invention is therefore characterized using two methodologies; a standard ethanol bubble point measurement technique is used to characterize a range of smaller pore sizes (from a nominal pore size of about 3 micrometers to about 150 micrometers) and a filtration technique is used to characterize a range of larger pore sizes (from greater than about 150 micrometers to about 3000 micrometers). The range of pore sizes over which these techniques can be used will vary depending on the material used to construct the TP device and its pore structure.

The range of smaller pore sizes from about 3 micrometers to about 150 micrometers is characterized using a standard bubble point measurement technique described in ASTM F316-86. Briefly, a representative portion at least 1 $cm^2$ is cut from the TP device. The representative portion should be chosen such that it is likely to include pores in the nominal pore size range of the TP device. One of several liquids of low surface tension and low vapor pressure may be used in this experiment; this includes but is not limited to water, petroleum distillate, denatured alcohol, ethanol and mineral oil. Complete wetting must be achieved prior to testing, and the liquid is chosen such that it can wet the sample. An appropriately designed holder must be used such that no liquid leaks past the sample. Increasing air pressure is applied upstream of the sample until air flow across the sample and through the level of liquid is first observed. The pressure at which this occurs is known as the bubble point pressure and defines the largest pore of the sample. The bubble point pressure may be converted to an equivalent pore diameter using the Washburn equation which is based on the premise of capillary pores having circular cross-section (ASTM F316-86). The pore size distribution may be further characterized by increasing the upstream pressure and recording the resultant air flow across both dry and wet membranes to obtain dry flow and wet flow curves. In order to show that the TP device is provided with two or more pores with less than a given bubble point pressure, the described bubble point experiment is repeated using another representative sample from the same TP device. This set of two experiments is repeated for an additional two TP devices. The higher of the two measured bubble point pressures for each TP device are then used to calculate an average bubble point pressure for the TP device. For example, two samples from each of three TP devices are found to have the following bubble point pressures: device #1—0.95 psi for the first sample and 1.0 psi for the second sample, device #2—0.9 psi and 0.85 psi, device #3—0.75 psi and 0.8 psi. The average bubble point pressure would then be the average of 1.0, 0.9 and 0.8 psi, i.e. (1.0+0.9+0.8)/3=0.9 psi.

For some TP devices it may not be possible to perform the bubble point test. For example, for TP devices with large pores (nominal pore diameter greater than about 150 micrometers) the liquid placed on the sample may, in some cases, flow through the pores thus prohibiting an appropriate bubble point measurement from being taken. If a bubble point test can not be carried out, the sample is assigned a bubble point pressure of 0 psi and the filtration method is performed to determine the maximum pore size. Subsequent to either a successful or unsuccessful bubble point test, the bead filtration test is performed.

The range of larger pore sizes from a nominal pore diameter of about 150 micrometers to about 3000 micrometers is characterized using a bead filtration technique. The bead filtration technique is based on the methods and practices described in ASTM F795-88. A representative portion at least 1 $cm^2$ is cut from the TP device. The representative portion should be chosen such that it is highly likely to include pores in the nominal pore size range of the TP device. The representative sample is flattened using such means as to cause minimal disruption to the pore structure and is mounted in an appropriate housing. For cases in which a representative sample can not be taken, the entire TP device may be mounted in a specially designed holder. For cases in which the representative sample can not be flattened a specially designed holder may be used. The important characteristic of the mounting process and holder design is that no flow is allowed to by-pass the sample. The liquid is chosen such that it completely wets the sample. Prior to mounting, the sample is pre-wet using either the liquid of the suspension or using a different liquid which is then replaced by the liquid of the suspension prior to starting the test. The solid beads are essentially spherical, essentially neutrally buoyant in the liquid of the suspension and have an essentially uniform size distribution. In addition, they are essentially unchanged in shape and size at any point in the suspension flow stream or as they pass across the sample. The beads constitute no more than 1% of the volume of liquid and at least 10 ml of suspension should be used. In addition an essentially homogenous suspension is maintained throughout the course of the experiment. The suspension is then allowed to flow through the sample either by gravity flow or by pumping the suspension across the sample or by applying air pressure above the surface of the suspension. If a pump is utilized, it should be chosen such that it does not grind the beads to alter the size distribution. The filtrate is collected and visually analyzed for evidence of beads which have passed across the sample. The experiment is repeated using progressively larger beads until the smallest bead which results in a filtrate devoid of beads is identified. The incremental change in bead diameter from one experiment to the next is chosen depending on the degree of accuracy required in the measurement of pore diameter. The pore diameter as measured by the filtration method is then defined as the diameter of the smallest bead that results in a filtrate devoid of beads. In most cases it is appropriate to wash the sample (using a back-washing technique or other appropriate cleaning technique which does not significantly alter the structure of the sample) between incremental changes in the bead diameter. For samples that can not be washed appropriately the series of tests is carried out without washing or a new representative sample is cut from the TP device each time the experiment is performed.

The test described thus far is only sufficient to determine the largest pore in the TP device. In order to show that the TP device is provided with two or more pores of less than a given diameter, the described series of experiments is repeated using another representative sample from the same TP device. This procedure is then repeated for two additional TP devices using two samples from each device. The higher of the two pore diameters measured for each TP device are then used to calculate an average pore diameter for the TP device. For example, two samples from each of three TP devices are found to have the following pore diameters as measured by the bead filtration test: device #1—450 micrometers for the first sample and 500 micrometers for the second sample, device #2—400 micrometers and 450 micrometers, device #3—400 micrometers and 350 micrometers. The average maximum pore diameter as measured by the bead filtration test would then be the average of 500, 450 and 400 micrometers, i.e. (500+450+400)/3=450 micrometers.

Using the characterization methodologies outlined above, the TP device of the present invention may be alternatively described in terms of two measurable variables; bubble point pressure and maximum pore size as determined by the bead filtration method.

The TP device of the present invention therefore has a plurality of pores such that it has an ethanol bubble point less than about 5 psi and a maximum pore size less than about 3000 micrometers as determined by the bead filtration method. Preferably, the TP device of the present invention has an ethanol bubble point less than about 0.32 psi and a maximum pore size less than about 1000 micrometers as determined by the bead filtration method. Most preferably the TP device of the present invention has an ethanol bubble point less than about 0.06 psi and a maximum pore size less than about 500 micrometers as determined by the bead filtration method.

The TP device is constructed from biocompatible materials. Examples of such materials include, but are not limited to non-degradable materials such as polytetrafluoroethylene, perfluorinated polymers such as fluorinated ethylene propylene, polypropylene, polyethylene, polyethylene terapthalate, silicone, silicone rubber, polysufone, polyurethane, non-degradable polycarboxylate, non-degradable polycarbonate, non-degradable polyester, polyacrylic, polyhydroxymethacrylate, polymethylmethacrylate, polyamide such as polyesteramide, and copolymers, block copolymers and blends of the above materials.

Alternatively, the TP device may be constructed of degradable materials such as non-highly crosslinked collagen, non-highly cross-linked hyaluronic acid, hydrolyzable polyesters such as polylactic acid and polyglycolic acid, polyorthoesters, degradable polycarboxylates, degradable polycarbonates, degradable polycaprolactones, polyanhydride, and copolymers, block copolymers and blends of the above materials.

Preferably, the porous material of the TP device is constructed of expanded polytetrafluoroethylene (ePTFE). ePTFE is an extremely inert and biocompatible material with a history of medical implant use. U.S. Pat. Nos. 3,953,566 and 4,187,390, the disclosures of which are incorporated herein by reference, teach methods for producing ePTFE suitable for use in the present invention.

The above materials may be made porous by any techniques known to those of ordinary skill in the art that will render the device capable of allowing cell and blood vessel through-growth into the space established by the device. Such techniques include, but are not limited to: sintering carefully controlled sizes of beads; combining the materials with a partially resorbable implant that would resorb or could be resorbed, in vivo or in vitro, to leave a porous structure; weaving or knitting fibers together to form a fabric-like material; using a foaming agent during processing to cause bubbles to form and leave pores as the material hardens; solvent/solution phase-separation; laser etching; ion beam etching; and particle leaching incorporating particulates such as salt or gelatin into the material structure and dissolving out the particles leaving porous voids.

The TP device is constructed in such ways and provided with such mechanical properties that it can be configured, prior to implantation, into a desired configuration and that it will substantially retain the desired configuration of the established space for a period of time necessary for substantially generating living bone or periodontal tissue within the space. Alternatively, the TP device may be constructed such that it can be configured during implantation. Establishing and retaining the desired established space within the body of the mammal may require the utilization of reinforcement means with the TP device. Examples of reinforcement means may take the form of struts, wires, or meshes. The reinforcement means are comprised of suitable biocompatible materials that are integrally constructed with the TP device. Such integral construction methods include, but are not limited to, lamination, casting and co-extrusion. Alternatively, the reinforcing means may be provided by placing a biocompatible porous matrix or framework within the established space, the framework providing the mechanical support for maintaining the configuration of the TP device.

The period of time necessary for substantially retaining the established space may vary depending on the type of living tissue (bone or periodontal tissue) to be generated, the volume and dimensions of living bone or periodontal tissue to be generated, and/or the specific TGF-Beta proteins provided. The mechanical characteristics required for substantially retaining the established space are of particular importance when degradable materials are used in the construction of the device or the reinforcement members. These degradable materials must not lose the capability of maintaining the desired established space prematurely.

At the time of implantation, the space established by implantation of the TP device does not contain living tissues of the mammal. At or soon after placement of the TP device, the space established within the body of the mammal by implantation of the TP device contains a carrier substance, either degradable or non-degradable, placed therein to provide the TGF-Beta protein. The carrier substance may additionally provide mechanical support to the TP device.

Additionally, materials may be placed in the established space that serve as a scaffold for the migration of cells and blood vessels originating from the living tissue of the mammal during the generation process. This scaffold may be as simple as blood coagulum which fills the space in the normal coarse of events following implantation of the TP device. Alternatively, the scaffold may be provided as part of the method and kit of the present invention and may include such known substances as collagen, hyaluronic acid, porous or particulate calcium phosphate or calcium carbonate.

A necessary component to this method of generating living bone or periodontal tissue with desired configuration within a mammal is by providing, within the space established by the device, one or more proteins from the Transforming Growth Factor-Beta Superfamily of proteins (TGF-Beta proteins) able to initiate, stimulate, and/or support, directly or indirectly, the growth and development of bone or periodontal tissues. The TGF-Beta proteins must be provided in ways and in forms that they are accessible to and able to stimulate the specific target cells, tissues, and physiological systems of the mammal necessary for generation of bone or periodontal tissue. The TGF-Beta proteins may be provided in a purified or partially purified form, having been produced outside the mammal being treated. The TGF-Beta proteins may be produced by a number of methods including, but not limited to, recombinant protein technologies or tissue extraction processes. Tissue extracted TGF-Beta proteins may be derived from xenogeneic, allogeneic, or autogeneic tissues including, but not limited to, bone, cartilage, dentin, liver, bone marrow or blood. The extraction method should remove a substantial portion of the cellular and non-TGF-Beta protein components of the tissue. Alternatively, the TGF-Beta proteins may be produced by cells that have been modified to produce the TGF-Beta proteins and which are placed within the space at the time of implantation. Cryopreservation is one method of providing the above-described cells.

TGF-Beta proteins known to stimulate tissue growth and development may act by stimulating certain cells to: 1) change to another type of cell (differentiation); 2) proliferate (mitogenesis); 3) migrate in a certain direction (chemotaxis); or 4) produce extracellular matrix substances such as collagen (matrix synthesis); or a combination of these effects. In addition, more than one TGF-Beta protein may provided to achieve different but complimentary stimulatory results; e.g. one TGF-Beta protein stimulates mitogenesis and another stimulates chemotaxis.

TGF-Beta proteins known to exert desired differentiation, mitogenic, chemotactic, or matrix synthesis effects on cells include, but are not limited to, Bone Morphogenetic Protein-2 (BMP-2) disclosed in U.S. Pat. No. 5,013,649 issued to Wang et al., and U.S. Pat. No. 5,385,887 issued to Yim et al., which are incorporated herein by reference.

In a preferred embodiment of the present invention, the TGF-Beta proteins are placed in a suitable carrier substance and positioned within a space established by the TP device. The carrier substance serves as a vehicle to provide the TGF-Beta proteins in ways and in forms that are able to stimulate the appropriate cells, tissues, and physiological systems of the mammal. Providing the TGF-Beta proteins from within a space established by the TP device achieves the most successful generation of living bone or periodontal tissue with desired configuration seen to date. The carrier substance may be either porous, non-porous, gel, or particulate (such as microspheres), and may be constructed from a variety of materials including but not limited to degradable and non-degradable polymers, collagen, hyaluronic acid and calcium salt materials such as tri-calcium phosphate, magnesium sulfate, calcium carbonate and hydroxyapatite ceramic. The carrier should not substantially block or interfere with the generation of bone or periodontal tissue within the space. Accordingly it is preferred that the TGF-Beta proteins are placed in a porous or particulate matrix that either degrades or occupies a small percentage or portion of the established space.

In some cases, the living bone or periodontal tissue that is generated within the established space originates from living tissue of the mammal. This process is dependent on the type of TGF-Beta protein provided, and the type and location of tissue (bone or periodontal tissue) desired. For example, it has been shown that it is possible, in a eight week time frame, to generate bone in the lower jaw of dogs and control the configuration of the bone generated. This has been accomplished by establishing a space between the existing bone of the jaw and the surrounding soft tissue using a polypropylene reinforced, configured, ePTFE TP device. The TGF-Beta protein, recombinant human Bone Morphogenetic Protein-2 (rhBMP-2), was applied to a purified degradable bovine collagen sponge carrier and placed within the space. The rhBMP-2 utilized was obtained from Genetics Institute, In Oambridge, Mass., and according to the teachings of U.S. Pat. No. 5,013,649, issued to Wang et al.; and U.S. Pat. No. 5,385,887 issued to Yim et al., which are incorporated herein by reference.

In other cases, it may be desirable to place cells, preferably harvested and isolated from the mammal being treated, that are precursors to either bone or periodontal tissue, within the space. These precursor cells and the TGF-Beta proteins provided determine the type of bone or periodontal tissue that will be generated. Undifferentiated mesenchymal stem cells are examples of cells that can be utilized to generate living bone or periodontal tissues. One method of providing these precursor cells is by cryopreservation.

During the implantation procedure, the TP device may be fixed in place to the surrounding tissue of the mammal with sutures, staples, tacks, screws, biocompatible adhesives, or other means known in the surgical art, of fixing implantable articles in the body. Alternatively, the device may simply be surgically placed within the mammal=s body without specific means of fixation.

The bone or periodontal tissue is generated at a site in a mammal where increase of living bone or periodontal tissue mass is desired. Alternatively the bone or periodontal tissue may be generated at a site distant from the site desired for increase in living tissue mass, and subsequently transferred to the desired site using surgical grafting methods known to those skilled in the art.

In a preferred embodiment, the TP device is constructed using sheets of expanded polytetrafluoroethylene (ePTFE). ePTFE identical in microstructure to the outer portion of GORE-TEX Regenerative Material Submerged Configurations (W. L. Gore and Associates, Inc., Flagstaff, Ariz.) is satisfactory as a starting material. Pores of 300 micrometer nominal diameter are constructed in the sheets using laser etching. The laser etched ePTFE sheets are reinforced by laminating to them a polypropylene mesh (Conwed 6065; Conwed Plastics, Inc. Minneapolis, Minn. U.S.A.). The reinforcement member is added both to allow configuring of the device and to aid in maintenance of the space established by the device. Optionally, the laminated ePTFE sheets can be configured by heat molding into desired configurations for such applications as the jaw bone ridge or long bones.

The ePTFE material used for construction of the laminated and configured TP devices exhibits the following porous characteristics: mean maximum pore size of 6.1 Tm as calculated from ethanol bubble point; and mean pore size of 1.7 Tm as calculated from mean ethanol flow pressure. Microscopic evaluation of the sheets show internodal distances of about 5 Tm to about 40 Tm (nominal 20–25 Tm) with the internodal spaces forming relatively tortuous channels through the wall thickness of the material. The laser etched pores have dimensions about 300 Tm in diameter and are located on centers about 0.8 mm apart in both X and Y axes. This results in approximately 11% of the surface area being occupied by the 300 Tm pores. The size and spacing of the laser-drilled holes was chosen to be offset with respect to the polypropylene mesh framework ensuring a significant portion of the laser-drilled holes are not blocked by the polypropylene mesh following lamination. The forced region of each sheet is then heat-molded into a permanent configuration using male and female aluminum dies. Spacing between the surfaces of the dies is maintained through the use of shims in order to prevent further distortion of the structure of the polypropylene mesh and possibly close off the laser-etched holes in the ePTFE.

In this embodiment, recombinant human Bone Morphogentic Protein-2 (Genetics Institute, Inc., Cambridge, Mass., and according to the teachings of U.S. Pat. No. 5,013,649, issued to Wang et al.; and U.S. Pat. No. 5,385,887 issued to Yim et al., each of which is incorporated herein by reference.) is combined with a bovine-derived porous collagen sponge that acts as a carrier for the rhBMP-2. HELISTAT® Absorbable Collagen Hemostatic Sponge (COLLA-TEC, Inc., Plainsboro, N.J.) is a satisfactory carrier.

The above mentioned TP device is surgically implanted such that a space is established within the body of a mammal. The absorbable collagen sponge that carries the rhBMP-2 is placed with the established space. The surgical wound is closed using standard surgical closure methods and articles.

Experiments with dogs show that living bone tissue, with desired configuration, is generated in large jaw bone defects utilizing the methods and articles of the above mentioned embodiment of the present invention. The generated living bone tissue substantially filled the space established by the pre-shaped TP devices at between 4 and 8 weeks after implantation. The TP devices used in these experiments were constructed from non-degradable expanded polytetrafluoroethylene membranes and polypropylene reinforcement mesh, and the TGF-Beta protein utilized was human recombinant Bone Morphogenetic Protein-2 (rhBM-2). Evidence from published literature suggests that the time frame for bone formation in response to rhBMP-2 is longer for humans than that for dogs.

In another embodiment, the TP device is constructed of biocompatible degradable materials. A starting material comprising porous non-woven web composed of poly (glycolide:trimethylene carbonate) (PGA:TMC) block copolymer processed according to the teachings of Hayes (U.S. patent application Ser. No. 08/942371 which is incorporated herein by reference) is satisfactory for this purpose. The web material has an ethanol bubble point value of greater than about 0.063 psi. This bubble point value corresponds to a pore size of less than about 150 micrometers. The PGA:TMC web material can be heat molded to a desired configuration for living bone or periodontal tissue generation. A further embodiment comprises the above mentioned PGA:TMC web starting material having ethanol bubble point mean value of greater than about 0.063 psi that is further laser etched to construct a plurality of through and through pores larger than about 200 micrometers and less than about 400 micrometers. Laser etching takes place following heat molding the web into the desired configuration. Further, a suitable carrier and TGF-J protein, for example rhBMP-2 in the absorbable collagen sponge, is placed into the space established by implantation of the TP device.

EXAMPLES

Introduction

Studies have demonstrated that alveolar bone and cementum regeneration appears critically dependent on the establishment of a space within the body of the mammal being treated. This space is established by the surgical placement of a barrier tissue-excluding (TE) membrane device that functions as a passive barrier to prevent ingrowth of fibrous connective tissue and establishes a space into which bone or periodontal tissues are desired to grow. It has been previously shown that in the canine critical-sized periodontal defect model described by Wikesjo and Nilveus (J Periodontal 1991;18:49–59), non-reinforced TE ePTFE membrane devices exhibit a tendency to collapse in response to pressure from the overlying soft tissue, with concomitant reduction in the volume of established space. TE devices are membranes with small pore size that substantially prevent tissue through-growth originating from soft tissues outside the boundary established by the membrane. Critical size defects do not spontaneously regenerate over the lifetime of the animal without some type of significant intervention. When collapse of the space is virtually complete, little or no bone regeneration occurs. In situations where collapse is incomplete and a limited volume of space is established, alveolar bone regeneration progresses and fills most of the space available within a four week period following surgery (Haney et al. J Periodontal 1993;883–890). In the presence of a larger volume space established with a shaped and reinforced membrane shell, the alveolar bone assumes a physiologic form adapting to the tooth surface averaging 75% of a 5 mm supraalveolar periodontal defect. The remainder of the wound space is filled by dense fibrous connective tissue (Sigurdsson et al. J Periodontal 1994;65:350–356). Inherent regeneration potential in critical size periodontal defects appears to be limited in amount although it can be significantly enhanced by TE membranes. In addition, the conformation of periodontal structures cannot be controlled by relying only on the inherent biological potential of the individual. No information has been available in this model on the inherent regenerative potential using membranes with pores large enough to allow tissue through-growth (tissue-penetrable-TP).

Example 1
Periodontal Regeneration with Tissue Exclusive and Tissue Penetrable Devices
Purpose The purpose of this study is to compare tissue-excluding (TE) and tissue-penetrable (TP) devices, for the ability to regenerate periodontal tissues in surgically created supraalveolar critical size defects. The devices are used to establish a space surrounding the teeth and surgically created defect. In this study, living tissue generation depends on the inherent biological regenerative potential of the subject. No exogenous TGF-Beta proteins or other bioactive molecules are placed in the space established by implantation of the devices in either experimental or control sites.

It is hypothesized that us a TP device, capable of allowing penetration of vascular structures and soft tissue cells into the established space, will result in regeneration of periodontal structures equivalent to TE devices.
Materials and Methods Six male beagle dogs (age 18–24 months, weight approximately 15 kg), exhibiting intact mandibular premolar dentition (P2, P3, P4) without crowding or evidence of periodontal disease, and obtained from a USDA approved dealer are included in the study.

Controls (TE) in the study utilize reinforced, preconfigured, ePTFE devices that are designed specifically for the canine supraalveolar critical size periodontal defects. These devices are provided with a microstructure that substantially excludes cells and blood vessels originating from the soft tissue located outside the boundary created by the device, from penetrating into the space established with the device.

Experimental (TP) sites are treated with similar ePTFE devices, designed to establish a space and having the same configuration as controls. Experimental devices are provided with relatively large (nominal 300 Tm diameter) through-and-through holes sufficient to allow through-growth of cells and blood vessels originating from the gingival soft tissue.

Pre-configured TE and TP reinforced ePTFE devices with defined three-dimensional shape are constructed by the following methods:

Expanded PTFE starting materials are manufactured following the methods described in Example 1 of U.S. Pat. No. 5,032,445, issued to Scantlebury et al. which is incorporated herein by reference. Using these starting materials, 5 cm×8 cm flat sheets of compressed ePTFE are produced following the procedures described in Example 8 of U.S. Pat. No. 5,032,445, issued to Scantlebury et al. which is incorporated herein by reference. The compressed ePTFE sheets exhibit density values of about 0.6 gm/cc to 1.4 gm/cc, and thickness of about 0.005 to 0.010 inches. Porosimetry testing of numerous lots return the following values for the ePTFE material used for construction of the laminated devices: mean maximum pore size of 6.1 Tm as calculated from ethanol bubble point; and mean pore size of 1.7 Tm as calculated from mean ethanol flow pressure. Microscopic evaluation of the sheets showed internodal distances of about 5 Tm to about 40 Tm (nominal 20–25 Tm) with the internodal spaces forming relatively tortuous channels through the wall thickness of the material.

A 24 mm×24 mm sheet of polypropylene scrim mesh (Conwed 6065; Conwed Plastics, Inc. Minneapolis, Minn. U.S.A.) is centered on the ePTFE sheet and the two materials are heat laminated together. The resulting polypropylene laminated ePTFE sheet is centered and clamped in a stainless steel frame clamp. The clamped flame is placed on a hot plate and the sheet heated to soften the polypropylene component. Once heated, the sheet is quickly placed in a press between bathtub shaped male and female aluminum dies and the dies closed. Spacing between the surfaces of the dies is maintained through the use of shims in order not further distort the structure of the polypropylene mesh. The heated sheet is allowed to cool thus locking the configuration of the sheet into the bathtub shape. The bathtub shaped area of each device has dimensions of approximately 24 mm in length and 10 mm in height and includes a circumferential skirt of non-reinforced ePTFE. The radius of the curvature at the apex of the bathtub is about 2 mm with the apex forming an arch shape having a diameter of approximately 4 mm. This shape is designed to generally recapitulate the height and arch shape of the alveolar ridge of the dog jaw and to adapt specifically to the defects in this animal model. These constructs comprise the TE device design.

To construct the TP devices identical 5 cm×8 cm sheets of compressed ePTFE are used as base material. Through and through holes are laser-drilled (Model 1720C, Universal Laser Systems, Scottsdale, Ariz. U.S.A.) in the central 24 mm×24 mm region of each ePTFE sheet. The drilled holes (pores) have targeted dimensions about 300Tm in diameter and are located on centers about 0.8 mm apart in both X and Y axes. This results in approximately 11% of the surface area of the 24 mm×24 mm area being occupied by the 300 Tm pores. Following laser-drilling of the holes, a 24 mm×24 mm sheet of polypropylene mesh is positioned directly over the laser-drilled area, heat laminated to the ePTFE sheet, and the reinforced area heat-molded as described above. The size and spacing of the laser-drilled holes is chosen to be offset with respect to the polypropylene mesh structure thus ensuring a significant portion of the laser-drilled holes will not be blocked by the polypropylene mesh following lamination.

All devices were packaged in EaglePac7 sterilization pouches and steam sterilized prior to implantation.

Small medical grade titanium alloy tacks (IMZ7 Bone Tacks, INTERPORE INTERNATIONAL. Irvine, Calif. U.S.A.), designed for these applications, were used to fix the devices to the bone of the mandible.

Preoperative Procedures

Each animal is prepared for surgery and prophylactic antibiotics (Cefazolin; 22–44 mg/kg iv) are administered within one hour of surgery and re-dosed every three hours during surgery. A non-steroidal anti-inflammatory agent (Banamine; 1 mg/kg iv) is administered immediately pre-surgery.

All surgical procedures are carried out with the animal under general anesthesia utilizing Telazol 3.0 mg/kg I.V. for induction followed by endotracheal intubation and maintenance with Halothane gas for the duration of the surgical procedure. Local infiltration with lidocaine:epinephrine (1:100,000 NOVOCOL Pharmaceutical of Canada, Inc., Cambridge, Ontario Canada) is given to reduce post operative pain and for hemostasis.

Operative Procedures

The first, second and third maxillary premolar teeth are surgically extracted, the fourth premolar is reduced in height to the level of the soft tissue, and exposed pulpal cavities are sealed (CAVIT®, ESPE, Seefeld/Oberbayem, Germany). This reduction of the maxillary dentition prevents potential of trauma from the maxillary teeth impinging on the experimental mandibular sites during healing. After extraction, the flaps are repositioned and sutured closed (GORE-TEX Suture CV5, W. L. Gore & Associates Inc., Flagstaff, Ariz.).

The supraalveolar critical size periodontal defect model used in this study, and its variations, are described by Wikesjo et al. (J Periodontal 1994;65:1151–1157). Critical size defects do not spontaneously regenerate over the lifetime of the animal without some type of significant intervention. Briefly, supraalveolar critical size periodontal defects are created around the $3^{rd}$ (P3) and $4^{th}$ (P4) mandibular premolar teeth in both right and left jaw quadrants in each animal. Crestal and sulcular incisions are made from the canine tooth to the $2^{nd}$ molar. From these incisions, buccal and lingual mucoperiosteal flaps are elevated, and the $1^{st}$ (P1) and $2^{nd}$ (P2) premolar teeth are extracted. Using chisels and water cooled high speed rotary burs, alveolar bone is removed from the flircation areas and around the circumference of the P3 and P4 to a level 5 mm to 6 mm below the cemento-enamel junction. The exposed root surfaces are carefully planed with surgical curettes, chisels, and high speed rotary diamonds to remove the tooth root cementum. The first mandibular molar (M1) is cut off at the level of the reduced alveolar bone found at the P3 and P4 sites and the bone height at the P2 location reduced to a similar level. This results in a clinical periodontal defect height of approximately 6 mm as measured from the cemento-enamel junction to the level of the reduced alveolar ridge. The crowns of the experimental teeth (P3 and P4) are cut off to approximately 1–2 mm coronal to the cemento-enamel junction, and the pulpal cavities sealed as described above.

Figure 8:
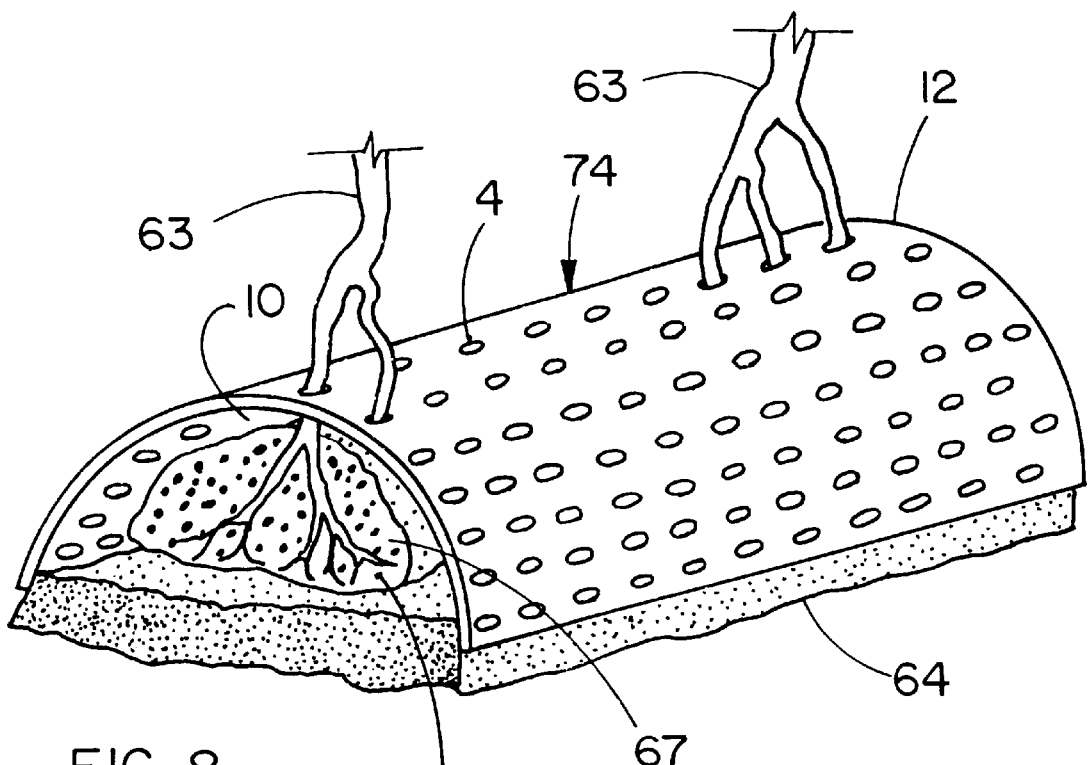
FIG. 8 illustrates an aspect of the present invention (74) placed in tissue of a host having host blood vessels (63) growing through holes (4) of the invention. A carrier matrix (67) having a TGF-Beta protein (69) is also shown placed within the delimited space (10) defined by the TP device (12) and the living tissue of the host (64).
Figure 9:
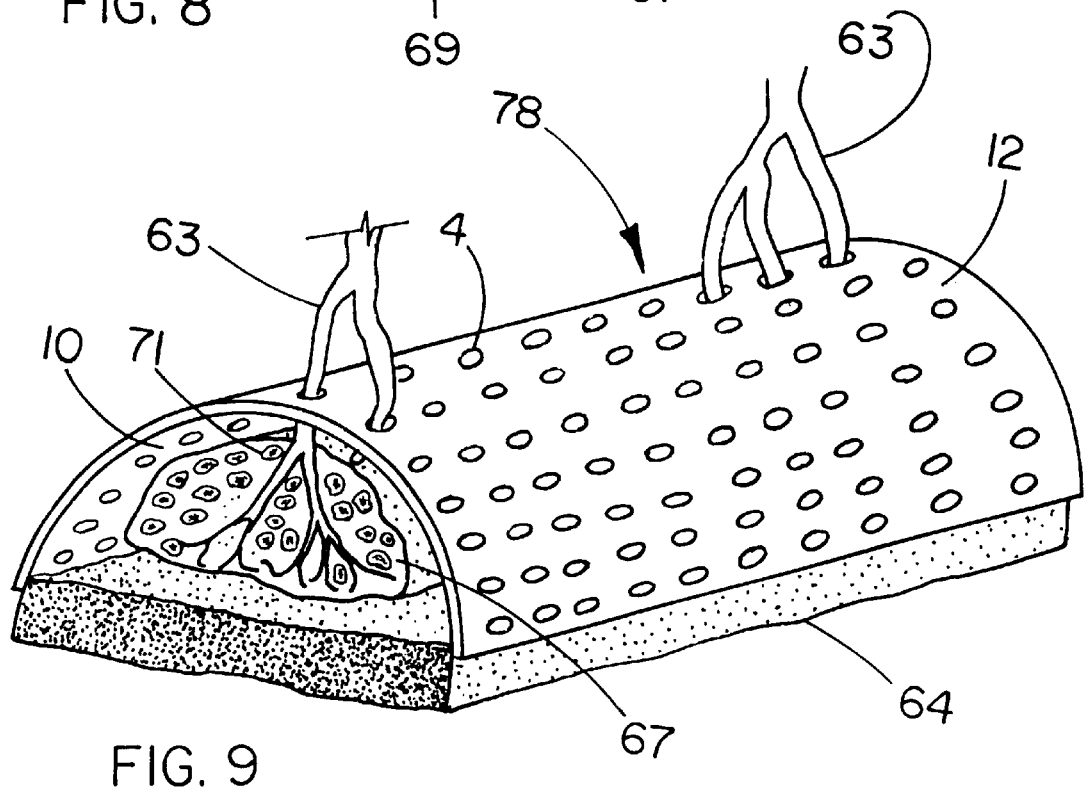
FIG. 9 illustrates an aspect of the present invention (78) placed in tissue of a host having host blood vessels (63) growing through holes (4) of the invention. A carrier matrix (67) having cells (71) modified to produce a TGF-Beta protein is also shown placed within the delimited space (10) defined by the TP device (12) and the living tissue of the host (64).
Figure 10:
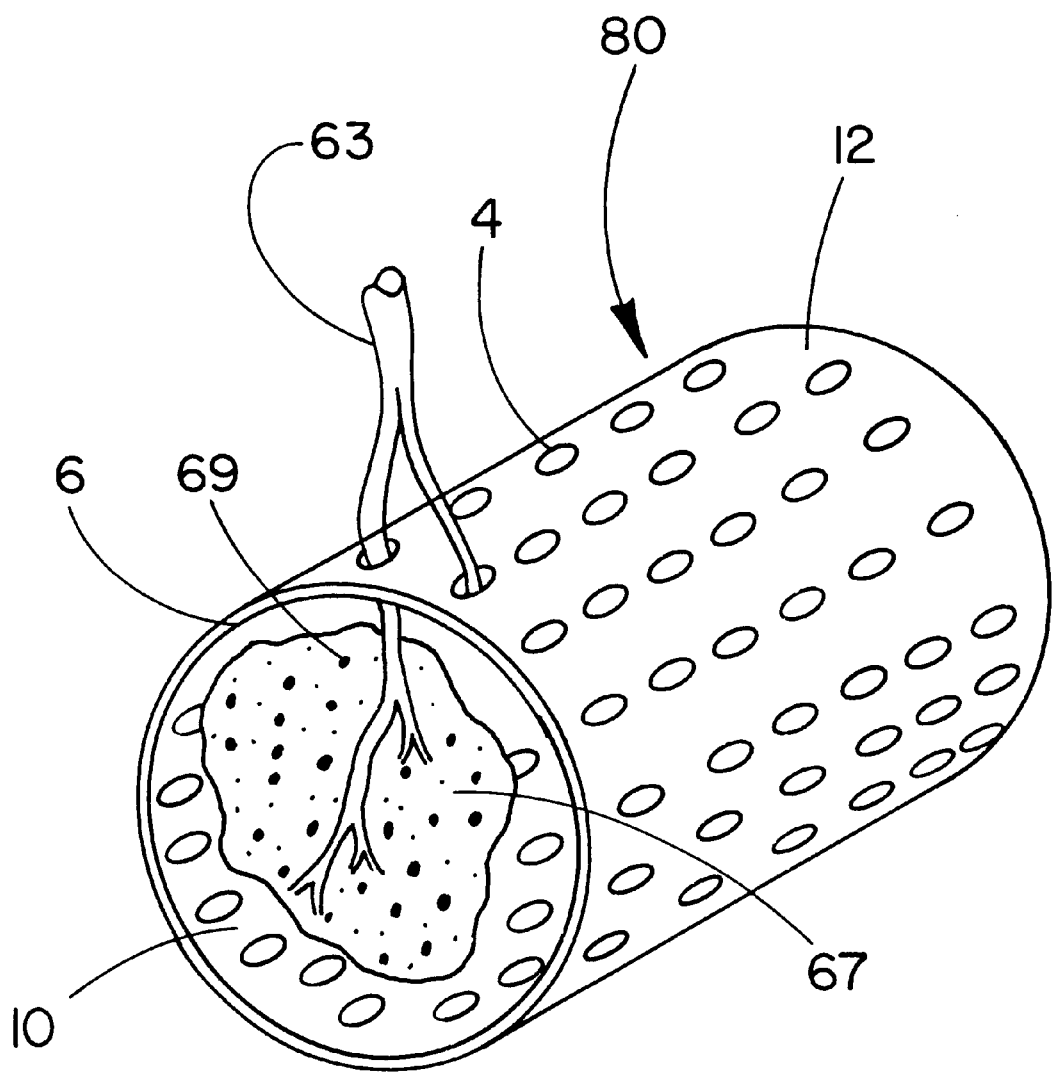
FIG. 10 illustrate aspect of the present invention (80) placed in tissue of a host having host blood vessels (63)

Following preparation of the defects, either a TE or TP device is positioned over the two experimental teeth. Proper placement of either construct establishes a space surrounding the teeth and periodontal defects. Implantation of the devices is accomplished by inverting the bathtub configuration and placing it over the teeth. The pre-shaped ePTFE membranes are trimmed to fit as closely as possible the individual sites, attempting to obtain close fit between the membrane and bone surface (FIG. 8). The devices are fixed to the intact portion of the jaw bone on the buccal side using small titanium alloy bone tacks designed for this purpose.

To ensure the formation of a blood clot in the space established by the membrane, venous blood is drawn from the animal and infused into the space established by the device. Venous blood is drawn aseptically from an intravenous catheter using a sterile syringe and needle. Approximately 3 ml of blood is drawn into the syringe, a fresh sterile needle is installed, and the blood injected underneath the membrane into the space.

Experimental conditions are alternated between left and right jaw quadrants in consecutive animals, with each animal receiving a tissue- exclusive and a tissue-penetrable treatment in contralateral quadrants.

Following completion of device placement and filling the established space with blood, the mucoperiosteal soft tissue flaps are mobilized by carefully cutting the periosteum near the base of the flaps, to allow tension-free flap apposition. The flaps are drawn over the positioned device and the flap margins adapted and sutured 3 to 4 mm coronal to the device (GORE-TEX Suture CV5, W. L. Gore & Associates Inc., Flagstaff, Ariz.).

Postoperative Care

Radiographs are obtained immediately postsurgery, and at four and eight weeks postsurgery.

Animals are fed a canned soft dog food diet the first 14 days postsurgery. Thereafter, the animals receive standard laboratory dog food pellets soaked in warm water until thoroughly soft. Analgesics are administered for postsurgery pain control. Broad spectrum antibiotics are administered for postsurgery infection control (Enrofloxacin, 2.5 mg/kg, im or iv, bid) for 14 days postsurgery. Gingival sutures are removed under sedation approximately ten days postsurgery.

Chemical plaque control is maintained by twice daily topical application of 2% chlorhexidine (Chlorhexidine Gluconate 20%, Xttrium Laboratories, Inc., Chicago, Ill.; 40 ml of a 2% solution) until gingival suture removal, and once daily thereafter (Monday thorough Friday) until completion of the study.

Harvest and Evaluation

The animals are anesthetized and euthanized at eight weeks postsurgery. Following euthanasia, teeth with surrounding soft and hard tissues are removed en bloc. Tissue blocks are fixed in 10% buffered formalin for three to five days, decalcified in 5% formic acid for eight to ten weeks, trimmed, dehydrated, and embedded in butyl methacrylate-paraffin. 7Fm-thick serial sections are cut in a buccal-lingual plan throughout the mesial-distal extension of the teeth. Every $14^{th}$ section is stained with Ladewig's connective tissue stain modified by Mallory allowing for observations at 100 Fm intervals.

Radiographs are taken of the blocks immediately following harvest. The specimen blocks are placed on their lingual surface directly on an unexposed radiographic dental film (Kodak Ultraspeed J DF-50, Size 4). A dental X-ray machine (Siemens Heliodent Model 3724861D3104) was set to 70 kV, 7 mA, at 0.32 second exposure time. The cone is positioned directly over the specimen at right angles to the film, and the film exposed.

New bone regeneration is measured by the following methods. A Mitutoyo metric dial caliper (accuracy "0.01 mm) is used to make the measurements directly from the radiographs. The following parameters are measured:

Defect height (D)—the distance from the parent or pre-existing bone crest (distinguished by relatively high radio-opacity) to the cemento-enamel junction (distinguished by the difference in radio-opacity at the point where the crown enamel meets the tooth root dentin). Defect height on mesial and distal surfaces of each tooth root are measured for a total of eight measurements for each quadrant (two teeth per quadrant, two roots per tooth, and two surfaces per root). The average defect height for the quadrant is calculated from the sum of these eight measurements.

Interproximal new bone height (IP)—the distance from the parent bone level to the most coronal extent of regenerated new bone (distinguished by the relatively low radio-opacity) in the space between the teeth.

An index (I) is calculated for the relative amount of interproximal bone regeneration for each tooth and each quadrant. This index is calculated by dividing the IP value by D for each tooth. This method allows for comparison of specimens taking into account possible differences in angulation of the tissue block relative to the direction of X-rays and/or the radiographic film. Mean T values, and standard deviations of the mean, are calculated for each experimental group (TP and TE) and each tooth group (e.g. TP;P3 and TP;P4).

Qualitative observations of the histological glass slides are also made. The most central stained section of each root for the third and fourth premolar teeth is identified by the size of the root canal. Sections were evaluated for bone regeneration.

Results
Clinical Observations

Four of the six animals in the study exhibit exposure of the TE devices, with three of the exposed quadrants requiring removal of the device due to inflammation and infection. Of the two unexposed devices, one exhibits swelling and edema throughout the eight week healing period.

Of the six tissue-penetrable devices, one became exposed, however, this device remained relatively non-symptomatic and in situ until harvest at the eight week time frame. The remaining five devices were non-exposed and non-symptomatic for the eight week healing period.

General Histological Observations

The following observations are made on sites that did not become exposed during the treatment period.

For all non-exposed sites, the space established by the devices is filled with tissue within the eight week time frame. The major components of the new tissue usually comprise variable amounts of vital bone continuous with the pre-existing bone and in close association with the tooth root surface, and moderately organized and vascukirized fibrous connective tissue generally located between the inner surface of the device and the tooth surface or new bone. Qualitatively, in all sites, the new bone tissue occupies less than 50% of the space established by the devices.

At least two of every three through-and-through holes in the ePTFE membranes shows large blood vessels (greater than 50 Tm in diameter) passing from the soft tissue peripheral to the device into the space established by the device.

Radiographic Evaluation

The results of the radiographic evaluation are shown in Table A.

In this model system, simply coronal positioning and suturing of the soft tissue flaps, without placement of either TE or TP devices, shows very limited potential for alveolar bone regeneration (Wikesjo et.al., J Periodontal 1994;65:1151–1157).

In this study only one of six TE sites remained non-symptomatic for the eight week healing period, with three of six sites requiring early removal due to exposure and infection. The single non-exposed, non-symptomatic TE site exhibited a new bone index of 0.96. The remaining five sites that exhibit some type of inflammatory complication show a range of new bone indices from 0.32 to 0.61 with a mean of 0.48.

This is consistent with a previous study using TE devices in this model, where investigators concluded that exposure and infection of TE sites compromise periodontal regeneration (Sigurdsson et.al., J Periodontal 1994;65:350–356). In addition, Sigurdsson et.al. found that non-compromised TE sites exhibited approximately 75% of alveolar bone regeneration (corresponding to a new bone index of 0.75).

In this study, five of six TP devices remained non-exposed and non-symptomatic for the eight week period, and exhibit new bone indices of 0.4 to 0.85 with a mean of 0.58. If the regenerative potential for non-compromised TP devices were similar to that shown for non-compromised TE devices, it is expected that the mean index of new bone for TP devices would approach at least 0.75.

Conclusions

These results suggest that treatment with TP devices have an increased regenerative potential compared to treatment without devices, and reduced regenerative potential compared to TE devices. These observations are consistent with the concept of Guided Tissue Regeneration that states that fibrous connective tissue cells originating from the gingival connective tissue have the potential to interfere with alveolar bone regeneration in periodontal defects. The TP devices, by virtue of the nominal 300 micrometer laser-drilled holes, allow fibrous connective tissue cells to have access to the space established by surgical implantation of the device. Neither TE nor TP sites regenerated periodontal tissue with configuration determined by the configuration of the device.

It also appears the use of TP devices decreases the likelihood of exposure related complications in this model system, compared with the TE devices.

TABLE A

NEW BONE REGENERATION INDICES
TISSUE PENETRABLE AND TISSUE EXCLUSIVE SITES
GROUP

| | TP | | | TE | | |
|---|---|---|---|---|---|---|
| K9# | I-P3 | I-P4 | Mean | I-P3 | I-P4 | Mean |
| 7591 | 0.93 | 0.77 | 0.85 | 0.34 | 0.32 | 0.32 |
| 7592 | 0.65 | 0.57 | 0.61 | 0.64 | 0.62 | 0.62 |
| 7593 | 0.45 | 0.47 | 0.46 | 0.46 | 0.41 | 0.41 |
| 7594 | 0.74 | 0.64 | 0.69 | 0.62 | 0.60 | 0.61 |
| 7595 | 0.43 | 0.38 | 0.40 | 1.02 | 0.90 | 0.96 |
| 7596 | 0.61 | 0.56 | 0.59 | 0.50 | 0.39 | 0.45 |
| Mean | 0.64 | 0.57 | 0.60 | 0.60 | 0.52 | 0.56 |
| "S.D. | "0.19 | "0.13 | "0.16 | "0.23 | "0.22 | "0.23 |

TP - Tissue-Penetrable devices
TE - Tissue-Exclusive devices
I - Index; Interproximal bone height) Mean defect height
P3 - mandibular 3$^{rd}$ premolar: P4 - 4$^{th}$ mandibular premolar Example 2
Membrane vs Space Distribution Delivery of the TGF-Beta Protein rhBMP-2
Purpose The objective of this experiment is to measure the release profiles of the TGF-Beta protein, rhBMP-2, from ePTFE and PGA:TMC membranes (membrane delivery). In addition, the membranes are treated with various agents to allow them to wet more easily, to change their surface chemistries, or to immobilize the protein through different types of bonds (e.g. ionic and covalent). The membrane release profiles resulting from these treatments are compared to those for a collagen sponge and a hyaluronic acid felt, which are chosen as appropriate carriers to deliver TGF-Beta proteins from a space established by a TP device (spatial delivery). The relative efficacy of spatial delivery versus membrane delivery is thus determined.

Materials and Methods

Material Description

Four materials were used as carriers in this release experiment: an expanded polytetrafluoroethylene (ePTFE) membrane, a membrane made from a poly (glycolide:trimethylene carbonate) (PGA:TMC) block copolymer (U.S. patent application Ser. No. 08/942371, issued to Hayes which is incorporated herein by reference), a collagen sponge (ACS; Helistat Absorbable Hemostatic Collagen Sponge, COLLA-TEC, Inc., Plainsboro, N.J.) and a hyaluronic acid felt (HA). The ePTFE membrane was manufactured according to the procedures described in Example 10 of U.S. Pat. No. 5,032,445, issued to Scantlebury et al. which is incorporated herein by reference. The PGA:TMC membrane was manufactured according to the teachings of Hayes (U.S. patent application Ser. No. 08/942, 371 which is incorporated herein by reference) in the form of a web structure with a fiber diameter of 30–35 Tm, a web density of 0.48 g/cc and a mean pore size of approximately 90 Tm.

Membrane Treatments

In addition to the four experimental groups described above, an additional six groups were included in this experiment. Both the ePTFE and PGA:TMC membranes were pre-treated in three ways: (i) soaked in isopropyl alcohol (IPA); (ii) coated with polyethylene imine (PEI), cross-linked by ethylene glycol bis[succinimidyl-succinate] (EGS), followed by PEI to create amino functional groups on the surface (Treated); (iii) coated with PEI, followed by EGS, followed by PEI and then adding the rhBMP-2 with sulfo-EGS to reversibly crosslink the rhBMP-2 (obtained from Genetics Institute, Inc., Cambridge, Mass., and according to the teachings of U.S. Pat. No. 5,013,649, issued to Wang et al.; and U.S. Pat. No. 5,385,887 issued to Yim et al., which are incorporated herein by reference.) to the surface (XL). Method (ii) provided ionic interactions between the membrane and the protein. Method (iii) produced hydrolytically labile covalent bonds between the membrane and the rhBMP-2. Steps (ii) and (iii) performed for ePTFE according to the teachings of Drumheller, U.S. patent application Ser. No. 08/660,698; filed Jun. 3, 1996; (companion application of PCT/US 90/01486) which is incorporated herein by reference. Steps (ii) and (iii) for PGA:TMC are performed according to the teachings of Cook et al. U.S. patent application Ser. No. 08/865,800, filed May 30, 1997 (companion application of PCT/US 97/09635) which are incorporated herein by reference.

Device Sizes

All of the ePTFE and PGA:TMC membranes were cut into 5×5 mm squares prior to loading of the rhBMP-2. The collagen sponge used in this study was in the form of an absorbable type I bovine collagen sponge (Helistat Absorbable Hemostatic Collagen Sponge, COLLA-TEC, Inc., Plainsboro, N.J.) that ws 3.4 mm in thickness. Each collagen sample was cut to 8×8 mm prior to loading of rhBMP-2. The hyaluronic acid felt (HYAFF 11p80) was supplied by Fidea Research Laboratories (Abano Terme, Padua, Italy) and was 1.5 mm in thickness. Each HA sample was cut to 28×4 mm prior to loading of the rhBMP-2.

Radio-Labeling of rhBMP-2

The uptake and release of rhBMP-2 from each device was measured using radioactivity counts. The rhBMP-2 was labeled with $^{125}I$ according to the following protocol. A 1.5 ml siliconized microcentrifuge tube (Fisher) was coated with Iodo-Gen (Pierce) reagent in advance by filling it with 200 mL of 20 mg/ml Iodo-Gen reagent and allowing it to dry overnight. The tube was stored at 4 alphaC. until used. On the day of the iodination, the reaction tube was rinsed with PBS (Gibco/BRL), then 30 mg of rhBMP-2 (7.5 ml of rhBMP-2 at 4 mg/ml), 5 mL of $Na^{125}I$ (1 mCi, Amersham), and 44 mL of PBS, pH 7.2 were added to the reaction vessel. The tube was gently agitated for 25 min., then the entire solution was transferred to a NAP-5 purification column (Pharmacia) which had been pre-equilibrated with PBS, pH 7.2. Ten 200 mL fractions were collected in separate microcentrifuge tubes by gravity drip, adding 200 mL of eluent at a time and waiting until the column had stop(dripping before proceeding. In order to identify the fractions with iodinated protein, 1 mL from each fraction was added to 33 mL of BSA solution (10 mg/ml in PBS), to,winch was added 333 mL of a trichloroacetic acid (TCA) solution (100 mg/ml in distilled water). The samples were incubated for 4 alphaC., forming a cloudy solution. The samples were centrifuged and the liquid fractions were transferred to a new tube and both solid and liquid fractions were measured for radioactivity using a gamma-counter. Samples with significant radioactivity (>95%) in the solid fraction were deemed to have been iodinated to an appropriate degree and the corresponding 200 mL eluent fractions were combined and stored at 4 alphaC. until needed. This iodinated rhBMP-2 was added in small quantities to the rhBMP-2 stock solutions which were used to load the devices tested in this study. Only sufficiently iodinated rhBMP-2 was used to achieve statistically measurable counts during the loading and release experiments.

Device Loading

All samples were run in triplicate. Membrane and pre-treated membrane groups were loaded with rhBMP-2 at different concentrations to achieve a similar initial loading of rhBMP-2 (16 Tg per sample) for each group. The untreated membranes were soaked in 240 mL of 4.0 mg/ml rhBMP-2 solution for 10 mins. The IPA samples were presoaked in IPA for 1 min then immediately transferred to distilled water for 1 min before being placed in 240 mL of 2.0 mg/ml rhBMP-2 solution for 10 mins. Both the Treated and XL samples were placed in 24 mL of 2.0 mg/ml rhBMP-2 solution for 10 mins. The ACS samples were soaked with 80 mL of 0.2 mg/ml rhBMP-2 solution and allowed to stand for 10 mins to allow incorporation of the protein within the sponge. The HA samples were soaked with 140 mL of rhBMP-2 at a concentration of 1.43 mg/ml and allowed to stand for 10 mins to allow binding of the protein to the felt.

Measurement of Uptake and Release

The radioactivity counts (measured in counts per minute (cpm)) from the collagen and HA samples were measured using a gamma-counter. Since the mass of rhBMP-2 added to these samples was known, these data were used to calculate a specific activity [cpm/Tg]. Immediately after loading of rhBMP-2, all samples were placed in separate glass test-tubes containing 0.5 ml of a pH 4.5 buffer. The radioactivity count from each sample was then measured d the specific activity was used to calculate the amount of rhBMP-2 loaded on each of the transferred samples.

Every 24 hrs, the samples were removed and placed in new glass test-tubes containing 0.5 ml of buffer. The radioactivity counts from the buffer left in the original test-tubes were measured and converted into a mass of rhBMP-2 released. The radioactivity counts from the sample in the new test-tubes were measured and converted into a mass of rhBMP-2 remaining on the sample. Both of these measurements were taken to ensure that the mass balance calculations were consistent. The specific activity value used to convert the radioactivity counts into a mass of rhBMP-2 was corrected each day to account for radioactive decay of the $^{125}$I-label.

The amount of rhBMP-2 released from each sample was then calculated as a percentage of the initial mass of rhBMP-2 loaded onto each sample.

Results

The results obtained from this release experiment are shown in Graph A below. For all eight membrane groups, the results were essentially identical. In excess of 93% of the rhBMP-2 loaded onto each membrane was released in the first 24 hrs. Less than 0.5% of the initial rhBMP-2 loaded was released from the membrane delivery devices over the preceding 24 hr period when sampled at three days. When a large percentage of the loaded agent is released in the initial portion of the desired release period, it is called a burst effect. In the application of the present invention, it is desirable to have sustained release of rhBMP-2 over a period of several days to achieve substantial induced bone formation in vivo. Since more than 93% of the rhBMP-2 was released in the first 24 hrs, the use of membrane delivery devices, such as those described here, would not be expected to provide rhBMP-2 (or other TGF-Beta proteins) to the host system for the several days necessary to achieve substantial bone or periodontal tissue formation. An acceptable rhBMP-2 delivery profile was not achieved using any of the membrane delivery devices tested.

In contrast, the initial 24 hr release from the collagen sponge and the HA felt only constituted 29.3% and 33.3% of the initial loading, respectively. Even after 7 days, 2.6% and 3.0% of the initial rhBMP-2 loaded were released from the collagen sponge and HA felt, respectively, over the preceding 24 hr period. When used as carriers for rhBMP-2 (or other TGF-Beta proteins) a collagen sponge or an HA felt may be expected to exhibit a biologically acceptable delivery profile sufficient to achieve substantial bone or periodontal tissue formation in vivo.

Conclusions

The collagen and hyaluronic acid carriers used in this study exhibited sustained release of a TGF-Beta protein (rhBMP-2) over a period of several days. Both the collagen and hyaluronic acid carriers may be expected to achieve an acceptable delivery profile conducive to generation of bone or periodontal tissue in vivo. In contrast, the membranes impregnated with a TGF-Beta protein (rhBMP-2) were not shown to achieve an acceptable delivery profile conducive to generation of bone or periodontal tissue in vivo.

Graph A: Release of rhBMP-2 from membranes and from space filling carriers. Release profiles are expressed as cumulative percent rhBMP-2 released from each device. Percentages were calculated based on the initial mass of rhBMP-2 loaded on each device and the values plotted are means for n=3.

Example 3

Purpose

The objective of this study is to determine if the configuration (size and shape) of alveolar bone associated with critical size supraalveolar periodontal defects, generated in vivo under the influence of the TGF-Beta protein, recombinant human Bone Morphogenetic Protein-2 (rhBMP-2), can be predictably controlled with the use of a pre-configured TP, ePTFE device when the inductive protein is distributed throughout the space established by the device.

It is hypothesized that implantation of a TP ePTFE space-defining device will allow interaction of rhBMP-2, when delivered from within the space established by the device, with the target host cells and tissues in such a way that generation of alveolar bone tissue can be predictably controlled resulting in formation of bone tissue with desired configuration.

Materials and Methods

Four adult male or female mixed-breed dogs (age 10–12 months, weight $ 20 kg) are obtained from a USDA approved dealer. The animals exhibit intact mandibular premolar dentition (P2, P3, P4) without crowding or evidence of periodontal disease. During the course of the study, each animal is identified by an implanted microchip.

TP devices, fabricated as described in Example 1, are used to establish a space surrounding the canine supraalveolar critical size periodontal defects.

rhBMP-2 (Genetics Institute, Inc., Cambridge, Mass., and according to the teachings of U.S. Pat. No. 5,013,649, issued to Wang et al., and U.S. Pat. No. 5,385,887 issued to Yim et al., which are incorporated herein by reference.) is used to induce bone formation. Sterile lyophilized rhBMP-2 is reconstituted and formulated in storage-stable buffer (MFR-842, Genetics Institute, Cambridge, Mass. And according to U.S. Pat. No. 5,385,887 issued to Yim et al. incorporated herein by reference) at a concentration of 0.2 mg rhBMP-2 per 1.0 ml of surgical implant volume. Absorbable type I bovine collagen sponge (ACS; Helistat Absorbable Hemostatic Collagen Sponge, COLLA-TEC, Inc., Plainsboro, N.J.) plus the buffer solution is used as a carrier for the bone inductive protein. All components of the implants are provided sterile for surgical implantation.

Small medical grade titanium tacks (IMZ® Bone Tacks, INTERPORE INTERNATIONAL, Irvine, Calif., U.S.A.), designed for these applications, are used to fix the shells to the bone of the mandible after positioning over the teeth following surgical defect induction.

This study utilizes the canine critical size supraalveolar periodontal defect model, and the preoperative, postoperative, and harvest and evaluation procedures in this study are identical to those described in Example 1.

All surgical procedures are carried out under with the animal under general anesthesia utilizing Telazol 3.0 mg/kg I.V. for induction followed by endotracheal intubation and maintenence with Halothane gas for the duration of the surgical procedure. Local infiltration with lidocaine:epinephrine (1:100,000; NOVOCOL Pharmaceutical of Canada, Inc., Cambridge, Ontario Canada) is given to reduce post operative pain and for hemostasis.

Operative Procedures

Surgical procedures follow those described in Example 1 with the following exceptions.

Each of the four dogs receive, in one mandibular quadrant, treatment with the TP device (TP), and about 0.4 mg rhBMP-2 (approximately 2 ml of 0.2 mg/ml rhBMP-2 solution) delivered in the ACS carrier (Group=TP+rhBMP-2+ACS). As controls, each contralateral quadrant receives TP+ACS+buffer (ACS wetted with 2.0 ml MFR-842 buffer) but without rhBMP-2. Within the group, treatments are alternated between left and right jaw quadrants in consecutive animals.

Distribution of the rhBMP-2 in the space established by the device is accomplished in the following way. Five strips of ACS (28 mm×10 mm×3.4 mm; dry dimensions) are cut from a larger sterile sheet using sterile instruments and technique. A centered 24 mm longitudinal slit is made in three of these strips. The remaining two strips are cut in half resulting in four shorter strips 14 mm in length. During surgery, 2 ml of rhBMP-2 (0.2 mg/ml) is dripped onto the ACS strips attempting to distribute the protein fairly evenly throughout the carrier. This results in a 0.4 mg total dose of rhBMP-2 that is delivered to the experimental sites. The volume of wetted ACS sponge is approximately 2 ml and slightly larger that the volume of the basin of the bathtub shaped device. The wetted strips are allowed to stand for at least 10 minutes to allow binding of the protein to the collagen. For sites that do not receive rhBMP-2, 2.0 ml of buffer are added to the ACS strips.

ACS strips are adapted to the tooth surfaces by placing one of the short strips in each exposed premolar furcation. A long strip is then adapted by slipping the longitudinal slit over the teeth and positioning it so that the strip is located along the surface of the bone and lateral and medial to the tooth root surfaces. A short strip is then placed in the space between the teeth and the second long strip is adapted on top of the first. The final layer involves placing a second short strip between the teeth and the third long strip over the teeth. When placement is complete the wetted sponge completely covers the root surfaces to a level at or above the CEJ, is somewhat wider than the jaw ridge, and extends 2–3 mm anterior to the P3 and posterior to the P4.

The pre-shaped TP ePTFE devices are trimmed to fit as closely as possible the individual sites attempting to obtain fairly close fit between the device and bone surface. Implantation of the devices is accomplished by inverting the bathtub configuration and placing it over the teeth and wetted ACS strips that have been adapted to the teeth., and fixed to the bone buccally with small sterile medical grade titanium alloy tacks (IMZ® Bone Tacks, INTERPORE INTERNATIONAL. Irvine, Calif. U.S.A.). Proper placement of the devices establishes a space surrounding the teeth and periodontal defects with the wetted ACS carrier filling virtually all the space inside the device.

Following completion of device placement the mucoperiosteal soft tissue flaps are mobilized and closed as described in Example 1.

Postoperative Care

Postoperative care follows those previously given in Example 1, with the exception that gingival sutures are removed between 5 and 8 days after surgery. In addition, chemical plaque control is maintained twice daily until suture removal. Once gingival healing has stabilized, chemical plaque control is terminated unless a clinical condition arises that requires control of infection or inflammation.

Harvest and Evaluation

Euthanasia, specimen harvest and radiography of specimens follows those procedures previously described in Example 1.

Following euthanasia, block sections including teeth, bone, soft tissues, and implanted materials are removed using sharp dissection and a reciprocating bone saw (Stryker) and radiographed to estimate bone regeneration. The block sections are rinsed in cool tap water and placed in 10% buffered formalin for a minimum of five days.

Specimens from two of the four animals are randomly picked and evaluated with computer-aided tomography scans (CT scans) using a General Electric Medical Systems CT scanner. For CT scan evaluation specimens are radiographically viewed laterally to determine where cross section cuts are to be made. The position of the cuts is identified and stored on the lateral images. The cuts used for comparison are made in a frontal plane between the teeth. Data from each scan is stored digitally on tape cassette and converted to radiographic film. Images are edge-enhanced for best resolution and each scan is stored and converted to radiographic film at a 1:1 linear ratio.

The standard x-ray films from each animal and CT scan images from randomly chosen animals are qualitatively compared. In both standard x-ray films and CT scan images, the new bone formed during healing is clearly identifiable by being less radio-opaque (radiographically less dense) than the original bone of the jaw. This phenomenon is normal for new bone formed in regenerative GTR procedures in the canine mandible. CT scan images from between the teeth are used for comparison.

For each specimen, the height of bone in relation to the CEJ of the teeth (expressed as a percentage of defect height) is determined from both the standard films and the CT scans. In addition, the cross-sectional shape of the new bone is determined from the CT scans. The location of the membranes is also identified by the presence of a continuous reticulate radiolucent line resulting from the presence of the polypropylene reinforcement mesh. All other tissues, including the soft tissues, show some degree of radio-opacity. The results of this comparison are shown in Table B; Group I.

Results

All animals evaluated exhibited non-complicated healing during the eight week in-life period. Radiographically controls (TP+ACS+buffer) show substantially less bone regeneration (approximately 25%) compared with the test sites (TP+ACS+rhBMP-2), all four of which exhibit 100% bone height formation, and virtually complete fill of the space established by the TP ePTFE devices (Table B). The new bone formation takes the arch shaped configuration of the devices, FIG. 14, Group I. Little to no bone formation is observable on the outside of the device in test sites.

TABLE B

RADIOGRAPHIC RESULTS

| EXAMPLE # | | GROUP | | HEIGHT (% of teeth/implants) | Normal Geometry (CT scan) |
|---|---|---|---|---|---|
| I | 3 | Teeth | TP + P + ACS | 100 | 2/2 Y |
|   |   |       | TP + ACS     | 25  | 2/2 N |
| II | 4 | Teeth | TP + P + ACS | 100 | 2/2 Y |
|   |   |       | P + ACS      | 100 | 2/2 N |
| III | 5 | Dental Implants | TP + P + ACS | 100 | 2/2 Y |
|   |   |       | TP + ACS     | 10  | 2/2 N |
| IV | 6 | Dental Implants | TP + P + ACS | 100 | 2/2 Y |
|   |   |       | P + ACS      | 90  | 2/2 N |

KEY
TP = Macroporous ePTFE TP Device
P = rhBMP-2
ACS = Absorbable Collagen Sponge Carrier for rhBMP-2
Note: N = 4 for all groups and results except for the CT data where N = 2.

Conclusions

The results of this study show that, within the eight week time frame, it is possible to predictably control the configuration of new alveolar bone formed by the activity of rhBMP-2 by establishing a space between the existing jaw bone and soft oral tissues using a thin walled, pre-configured TP ePTFE device and distributing the bone inductive protein throughout the space. It important that the new alveolar bone formed exhibits fairly precisely the configuration of the space established by the TP ePTFE device. It is also of importance that this result is obtained in all four individuals in the study.

Example 4

Purpose

The objective of this study is to determine if the configuration of alveolar bone, associated with critical size periodontal defects and generated in vivo under the influence of the TGF-Beta protein, rhBMP-2, can be controlled with the use of a TP ePTFE device when the inductive protein is placed within, but not distributed entirely throughout, the space established by the device. Additionally, results obtained from TP+rhBMP-2+ACS sites are compared with sites treated only with rhBMP-2+ACS without placement of a TP device.

Materials and Methods

Four adult male or female mixed-breed dogs (age 10–12 months, weight $ 20 kg) are obtained from a USDA approved dealer. This study utilizes the canine critical size supraalveolar periodontal defect model, and the preoperative, postoperative, and harvest and evaluation procedures in this study are identical to those described in Example 1. TP devices, as described in Example 1, are used to establish a space surrounding the supraalveolar critical size periodontal defects.

Operative Procedures

All operative procedures follow those described in Example 3 with the following exceptions.

Each animal in this study receives TP+ACS+rhBMP-2 (0.4 mg) in the test quadrant, however, the protein is not distributed throughout the space provided by the device at the time of implantation. Rather, 0.4 mg rhBMP-2 is placed within the space but delivered in a volume less than one half of the available space. Briefly, using sterile procedures, three strips of ACS are cut from a sterile larger sheet. Two of these strips have dimensions of approximately 12 mm×10 mm×4 mm. The dimensions of the third strip is approximately 24 mm×10 mm×4 mm. A centered longitudinal slit approximately 20 mm in length is cut into this longer strip to allow positioning over the two experimental teeth. Prior to placement of the ACS sponge strips into the experimental sites, rhBMP-2 solution (240 Tl:1.43 mg/ml) is dripped onto the strips and allowed to stand for at least 10 minutes to allow binding of the bone inductive protein to the collagen substrate. After wetting, the short strips are placed into the furcations of the experimental teeth, and the longer strip is slipped over the teeth, similar to the placement process described in Example 1. TP ePTFE devices are trimmed to fit, placed over the wetted ACS strips and teeth, and fixed in place as previously described. The volume of the wetted strips is not large enough to completely fill the space provided by the TP device. The strips therefore provide a source of the bone inductive protein located within the space, but is not initially distributed throughout the space.

In contralateral quadrants (control), strips of sterile ACS are prepared as described in Example 3. 2 ml rhBMP-2 (0.2 mg/ml) is dripped onto the strips and allowed to stand for at least 10 minutes. The wetted strips are adapted to the teeth as described in Example 3, however, no TP devices are placed over these defects. The volume of the wetted strips is approximately 2.4 ml.

After placement of the implanted materials, the soft tissue flaps are mobilized and closed as previously described in Example 1, and the sites allowed to heal for 8 weeks.

Harvest and Evaluation

Harvest procedures follow those described for Example 1. As described in Example 3, the standard x-ray films from each animal and CT scan images from two animals randomly chosen are qualitatively compared. CT scan images from between the teeth are used for comparison. In sites with rhBMP-2+ACS, but without protection by TP devices, this location is most protected from mechanical trauma and soft tissue pressure, and therefore favors best outcomes for the controls.

Results and Conclusions

All animals evaluated exhibit non-complicated healing with the exception of some ACS+rhBMP-2 sites which show fluid-filled lesions in the soft tissue.

TP+ACS+rhBMP-2 sites do not develop these lesions. All lesions eventually resolve and the tissue health returns to normal prior to sacrifice.

In all cases sites treated with the TP device and rhBMP-2 (TP+ACS+rhBMP-2) show bone regeneration to a level of 100% or greater of the defect height (Table B). Bone tissue has largely filled the space within the TP device when rhBMP-2 is present, even though the protein is not completely distributed throughout the established space (Table B, Group II). The shape of the bone formation induced by the protein takes on the arch shaped configuration of the devices and the configuration is controlled by the shape of the device, with little to no bone formation taking place outside the space established by the device.

Sites treated with rhBMP-2+ACS show bone regeneration to the level of the CEJ or above ($\geq$100% of defect height) (Table B, Group II). However, the cross-sectional shape of the ridge varies considerably from site to site, and the overall arch shape of a normal alveolar ridge is not predictably attained (FIG. 14, Group II). Instead, the cross-sectional shape of the regenerated bone is roughly triangular.

Conclusions

Generation of viable bone with a predictable configuration is accomplished by establishing a space with implantation of a TP device, and placement of a bone inductive protein within the space established. This occurs when the protein is distributed through a portion of the space available. Predictable control of the configuration of bone is not attained by placement of the bone inductive protein and carrier alone.

Example 5

Generation of Bone in Supraalveolar Peri-Implant Defects

Purpose

The purpose of this study is to evaluate the ability to predictably generate alveolar bone with controlled configuration, in canine critical size supraalveolar peri-implant defects using a TP device and the TGF-Beta-protein, rhBMP-2, where the bone inductive protein is distributed throughout the space established by implantation of the TP device.

Materials and Methods

Preoperative, postoperative and harvest procedures follow those described in Example 1, with the exception that the specimen blocks are embedded in methylmethacrylate polymer, and histological sections are prepared by sawing and grinding.

Surgical Procedures

Maxillary dentition is reduced as described in Example 1. Supraalveolar, critical size peri-implant defects are surgically prepared in the mandibular premolar region in left and right jaw quadrants in four adult mixed-breed hounds.

Gingival flap preparation is accomplished as described in Example 1. Alveolar bone is removed to a level of 6 mm from the CEJ around the circumference of the mandibular premolar teeth with chisels and water cooled rotating burs. The $1^{st}$, $2^{nd}$, $3^{rd}$, and $4^{th}$ mandibular premolars teeth are extracted and the first molar is cut off at the level of the reduced bone.

In each quadrant, three custom made 10 mm threaded cylindrical titanium dental implants (3.25 mm Internal Hex MINIPLANT, Implant Innovations Inc., Palm Beach Gardens, Fla.) are placed 5 mm deep into the remaining alveolar bone using standard minimally traumatic methods.

This results in the upper 5 mm of each dental implant being located above the reduced bone level. The exposed dental implant surfaces are here termed supraalveolar, critical size peri-implant defects. Actual dimensions of the exposed implant surfaces are measured with a periodontal probe and recorded in the animal's chart.

A treatment design for test and control quadrants identical to that described for periodontal defects in Example 3 is applied to the peri-implant defects. The test quadrants receive TP+ACS+0.4 mg rhBMP-2 (2.0 ml @ 0.2 mg/ml) and the contralateral controls receive TP+ACS+buffer (2.0 ml). In this study design, the bone inductive protein is distributed throughout the space provided by the TP device.

Tissue closure is accomplished as explained in Example 1.

Evaluation

The standard x-ray films from each animal, and CT scan images from two randomly chosen animals, are qualitatively compared as described in Example 3. CT scan images from between dental implants are used for comparison.

Results

All animals show non-complicated healing. Radiographic analysis show that peridental implant defects treated with TP+rhBMP+ACS exhibit complete fill of the space established by the device with mineralized tissue (FIG. 14, Group E) and 100% or greater of the dental implant height (Table B, Group III). The configuration of the new bone is arch-shaped in cross-section similar to the configuration of the TP devices (Table B, Group III). Control sites (TP+ACS+buffer) exhibit mineralized tissue growth to only about 10% of the dental implant height and available space established by the device (Table B and FIG. 14, Group III).

Qualitative histological observations of test sites (FIG. 15A) confirm the radiographic findings with new bone formation occupying the majority of the space provided by the TP device. In general, mineralized bone trabeculae occupy the majority of the space established with some variation of density. In addition there are typically very thin (# about 150 Tm) plates of bone located on the outer surface of the device in localized areas and a thin (# about 300 Tm) layer of immature fibrous connective tissue located between the new bone trabeculae located in the established space and the inner surface of the device. Large blood vessels are commonly observed penetrating the 300 Tm laser-etched holes in the ePTFE material. It is estimated that greater than 80% of the space established by the devices is occupied by bone tissue. Control sites show substantial height of bone formation, however, the configuration is roughly triangular in cross-section indicating inability to control the configuration of generated bone tissue (FIG. 15B).

Conclusions

It is concluded that by establishing a space with a pre-configured TP ePTFE device, and distributing rhBMP-2 throughout the space, viable bone tissue in the configuration of the space is predictably formed by eight weeks in this model.

Example 6

Purpose

The purpose of this study is to evaluate the ability to predictably generate bone in a controlled configuration in canine critical size supraalveolar peri-implant defects using pre-configured TP devices and rhBMP-2, where the bone inductive protein is placed within the space established by implantation of the TP device, but not distributed entirely throughout the space. The results of the TP device and rhBMP-2 treated sites are compared to sites where rhBMP-2 is administered without the benefit of a TP device.

Materials and Methods

Preoperative, postoperative and harvest procedures follow those described in Example 1, with the exception that the specimen blocks are embedded in methylmethacrylate polymer, and histological slides prepared by sawing and grinding.

Four adult mixed-breed hounds are used in this study. Maxillary dentition is reduced as described in Example 1. Critical size supraalveolar peri-implant defects are prepared in the mandibular premolar regions bilaterally, as described in Example 5. TP devices identical to those described in Example 1 are used to establish a space surrounding the surgically prepared peri-implant defects.

Test quadrants receive TP+rhBMP-2+ACS (0.4 mg total dose). The TP+rhBMP-2+ACS constructs are prepared as described in Example 4, with the wetted ACS strips filling less than half of the space provided by the membrane.

Control quadrants receive ACS+0.4 mg rhBMP-2 (0.4 mg in approximately 2.4 ml wetted ACS volume as described in Example 1), but do not receive TP device covers. After placement of the implanted materials, the soft tissue flaps are mobilized, apposed, and sutured as described in Example 1. The sites are allowed to heal for 8 weeks.

The standard x-ray films from each animal, and CT scan images from two randomly chosen animals are qualitatively compared as described in Example 3. CT scan images from between the dental implants are used for comparison. In the control sites with rhBMP-2 but without membranes this location is most protected from mechanical trauma and soft tissue pressure, and therefore favors best outcomes for the controls.

Results

All animals evaluated exhibited non-complicated healing with the exception of some ACS+rhBMP-2 sites which develop fluid-filled lesions in the soft tissue. These lesions eventually resolve and the tissue health returns to normal prior to sacrifice.

All test sites (TP+BMP+ACS), with the exception of one animal, exhibit new bone formation throughout the space provided by the TP device and 100% or greater of the implant defect height (Table B, Group IV). The single exception to is an animal that exhibits what might be described as an exuberant response to the protein with both test and control quadrants forming a very large volume of bone, apparently with the architecture of a hollow shell. This animal was not evaluated with CT scans and it is unknown why this individual exhibits this apparently aberrant response.

Control sites treated with ACS+rhBMP-2 show considerable height of bone formation (80–100% of implant height, Table B, Group IV), however, the jaw ridge has a knife edged appearance and the configuration of new bone does not have the characteristic arch shape of an alveolar ridge (FIG. 14, Group IV). Clinically this is most evident on the lingual aspect where three quadrants indicate that a significant part of the implants are apposed by soft tissue rather than bone.

Qualitative histological observations largely confirm the radiographic findings. In all test sites new bone formation occupies the space established by the TP devices, including the one site with bone formation in the soft tissue outside the boundary of the device. In three of the test sites bone formation is largely confined to the established space with only localized and thin bone plates located adjacent to the outside device surface as previously described in Example 5. Once again, there is a thin layer of immature fibrous connective tissue interposed between the new bone trabeculae in the space and the inner device surface, and it is estimated that greater than 80% of the area of the space is occupied with bone tissue. The one test site exception mentioned in the radiographic analysis does show substantial bone formation beyond the boundary of the device in the soft tissue region as well as bone formation within the established space.

Three of the four control sites (ACS+rhBMP-2) exhibit limited and variable bone formation located primarily on the buccal (cheek) surface of the implants and having a relatively thin knife edge appearance between the implants. Lingual (tongue) surfaces of the dental implants are generally apposed by fibrous connective tissue of the gingiva It is estimated that new bone formation is less than about 20% of that observed in the test quadrants. The remaining control site shows a relatively large volume of bone formation having the form of a hollow shell with a relatively thin (# about 1 mm) mineralized bone exterior and the interior of the shell having a cyst-like appearance. The dental implants are located within the cystic region. The height of bone in this site is greater than 100% of the dental implant defect height.

Conclusions

The results of this study show that using a TP ePTFE device to establish a space and providing a bone inductive protein within, but not distributed entirely throughout that space enables the predictable generation of bone tissue with controlled configuration. The configuration of new bone is largely determined by the configuration of the space established by the device. The single exception to this is found in a animal that showed an apparent aberrant response in the control site as well, and may therefore be explained as an unusual response by a single animal which may have been abnormally sensitive to the protein.

General Conclusions: From Examples 1,3,4,5, and 6

When no rhBMP-2 is provided in the established space, use of TP devices appears, at best, to achieve no better regenerative result than TE devices. In fact, the evidence from Example 1 suggests that while TP devices appear to enhance periodontal bone regeneration, compared to published information from the canine supraalveolar critical size periodontal model without device placement, regenerative capacity may be somewhat decreased compared to treatment with TE devices. In neither TP nor TE sites without rhBMP-2 is the configuration of regenerated periodontal bone controlled (Example 1).

In contrast, sites treated with the TP device and rhBMP-2, whether or not the protein was distributed entirely throughout the established space, show bone regeneration to a level of 100% of the tooth or dental implant height (Table B). Of greatest importance is the observation that bone tissue had largely filled the available space with the TP devices when rhBMP-2 was placed within the space (Table B, and FIG. 14). Significantly the shape of bone formation induced by the protein was determined by the shape of the device, and therefore the space, with little to no bone formation having taken place outside the space established by the device. This was true for both periodontal and peri-implant sties. Thus, the shape and volume of the new bone formed by the activity of the rhBMP-2 was determined closely by the configuration of the device. Significantly, in 15 out of 16 sites, the shape of bone formation induced by the protein exhibits the arch configuration provided by the configuration of the TP ePTFE devices. It is estimated that in the 15 sites with controlled configuration, greater than about 80% of the established space is newly generated living bone tissue.

Control sites treated with TP devices and ACS but without rhBMP-2 show substantially less bone regeneration compared with either the TP+ACS+rhBMP-2 sites, or the ACS+rhBMP-2 sites (Examples 3, 4, 5, and 6). This was true for periodontal defects (25%) and peri-implant sites (10%).

Periodontal sites treated with rhBMP-2 +ACS, but without TP devices show bone regeneration to the level of the CEJ or above. However, the cross-sectional shape of the ridge varies considerably from site to site, the volume of new bone formed is generally less than sites treated with tp ePTFE devices and rhBMP-2, and the overall arch shape of a normal alveolar ridge is not predictably attained.

Dental implant defects treated with rhBMP-2 +ACS show considerable height of bone formation (80%–100% of implant height) but the new bone ridge has a knife edged configuration, and does not attain proper alveolar ridge configuration.

These studies show that placing rhBMP-2 within a space established by a TP ePTFE device predictably results in virtually complete fill of the space in a relatively short period of time with new bone tissue in very nearly the exact size and shape defined by the device boundary. The percentage of successful control of new bone configuration for Examples 3, 4, 5, and 6 is 94% (15 of 16 sites). In control sites, new bone that formed under the influence of rhBMP-2, but without the benefit of TP devices, exhibits variable volume and shape.

These results imply that with use of methods and articles of this invention, virtually any skeletal shape can be attained and is dependent on the configuration of the space established by the device.

Example 7

Generation of Bone in Canine Critical Size Segmental Ulnar Defects

Purpose

The objective of this study is to predictably generate bone with controlled configuration in canine critical size ulnar defects, thereby reconstructing bridging of bone ends with the dimensions of the bone removed by surgical resection.

Materials and Methods

Four systemically healthy adult male or female mixed breed dogs weighing more than about 20 kg are used in this study. The animals are systemically healthy and identified by implanted microchip.

Sheets of polypropylene reinforced TP ePTFE approximately 4.5 cm×6 cm are constructed in a manner similar to that described in Example 1. rhBMP-2 at a concentration of 0.2 mg/ml in ACS carrier is used for inducing bone formation. Standard stainless steel bone plates and screws are used for internal fixation of the ulna during the healing period. Small bone screws are used for fixation of the TP ePTFE device.

Preoperative Procedures

Following acclimation, each animal is prepared for surgery and anesthetized as described in Example 1. Each animal is placed in lateral recumbancy and the skin directly over the mid-shaft of the ulna is shaved, disinfected, and draped with sterile covers.

Operative Procedures

An incision is made in the skin directly over the ulnar mid-shaft and sharp and blunt dissection is made to the bone surface. All muscle attachments are carefully elevated from the mid-shaft region for a distance of approximately 6–8 cm using periosteal elevators. Using water cooled high speed rotary instrumentation, a 3.5 cm segment of the ulnar diaphysis is removed at approximately mid-shaft. This results in a segmental defect approximately 22 times the diameter of the diaphysis and represents a critical size defect. The diameter of the segment removed is measured at its mid-point for comparison with new bone formed during treatment.

In test sites, holding the ulna in position, the sheet of TP ePTFE is placed underneath the segmental defect now present in the ulna. Approximately 2.5 ml of 0.2 mg/ml rhBMP-2 solution is dripped onto ACS carrier to give approximately 3.0 ml of volume, and the wetted carrier is allowed to stand for about 10 minutes. Test sites receive approximately 0.5 mg total dose of rhBMP-2. The wetted carrier is placed into the defect in the bone and the TP ePTFE sheet is wrapped around the bone and carrier overlapping the bone ends by approximately 1.0 cm and overlapping one edge over the other by approximately 1 cm. This encloses and establishes the boundaries of the defect space now filled with the carrier. The bone ends of the ulna are positioned and fixed in place with standard bone plates and screws and the TP ePTFE sheet device is fixed in place with small bone screws.

Control limbs receive approximately 0.5 mg rhBMP-2 in ACS carrier, and bone plate fixation, but with no space establishing TP ePTFE device. The soft tissues are closed in layers using absorbable sutures and the skin closed with surgical staples or sutures.

Antibiotics and analgesics are administered for prevention of pain and the sites are allowed to heal for 24 weeks.
Harvest and Evaluation Animals are anesthetized and euthanized at 24 weeks post-operative. Ulnae are carefully dissected free removing the bone plates but leaving any soft tissue and TP ePTFE devices intact. Each ulna is radiographed and CT scans are taken at 1 cm intervals through the defect region.
Results It is expected that test sites treated with TP ePTFF devices and rhBMP-2 show compete bridging of the defects and virtually complete ($\geq 80\%$) fill of the space established by the devices with new bone tissue. The diameter of new bone formed in these defects is within 80% or greater of the diameter of the original diaphysis. In addition it is expected that there is little to no bone formation on the exterior surface of the devices.

Control sites are also expected to show bridging of the defects, however, it is expected that there will be substantial variability in the configuration of new bone that is formed, with the general observation that the new bone formed is of lesser diameter than the diameter of the diaphysis of the original bone.
Conclusions It is concluded that use of a space establishing TP ePTFE device in conjunction with a bone inductive protein shows predictable generation of bone bridging canine critical size defects with control of configuration of new bone formed.

Example 8

Purpose

The objective of this study is to determine if the configuration of periodontal bone, generated in vivo under the influence of the TGF-Beta protein, rhBMP-2, can be predictably controlled with the use of a pre-configured TP device constructed from poly(glycolide:trimethylene carbonate) (PGA:TMC) block copolymer web, when the protein is distributed throughout the space created by the device.
Materials and Methods PGA:TMC membrane webs are constructed using the process described by Hayes (U.S. patent application Ser. No. 08/942371 which is incorporated herein by reference). These webs are formed into bathtub configurations using heated aluminum molds having the same configuration described in Example 1. The heat forming also sets the configuration of the devices. The dimensions of the molded portion of the devices are approximately 24 mm in length× 10 mm in height with a 4 mm diameter at the apex of the arch. After heat molding, 300 Tm through and through holes are laser drilled (Model IROC, Universal Lazer Systems, Scottsdale, Ariz. USA) in the sides of the bathtub. There are three rows of holes in each side of the device with the rows being approximately 24 mm in length and the holes are located on 1.75 mm centers. Each device has a circumferential non-laser drilled skirt. The pre-configured, laser-drilled devices are packaged in foil pouches and gamma sterilized prior to implantation.

Nine adult male beagle dogs are used in this study. In each animal critical size periodontal defects are created bilaterally in the mandible following the operative procedures described in Example 1.

Preoperative, operative, postoperative, and harvest procedures are carried out as described in Example 1.

In this study, hyaluronic acid (HA; HYAFF 11p80, Fidea Research Laboratories (Abano Terme, Padua, Italy) formulated into a felt is used as a carrier for the bone inductive protein. Studies indicate that the HA exhibited an uptake and release profile for rhBMP-2 similar to the ACS (Graph A, Example 2).

For test quadrants, HA+rhBMP-2 implants are prepared using sterile procedures. 2.0 ml rhBMP-2/buffer solution (0.2 mg/ml) is dripped onto the HA strips and allowed to stand for at least 10 minutes. The total rhBMP-2 delivered to the defect is 0.4 mg. After preparation of the defects, the wetted strips are adapted to the teeth as described in Example 3.

The TP PGA:TMC devices are trimmed to fit the defects, positioned over the teeth and wetted HA, and fixed in place to the bone with small titanium tacks as described in Example 1. The wetted HA fills virtually all the available space within the PGA:TMC device.

Contralateral quadrants receive HA strips wetted with 2.0 ml buffer without rhBMP-2, and are fitted with TP PGA:TMC devices.

CT scans of harvested blocks are obtained as described in Example 3. Qualitative observations of these scans are presented.
Results Two of the animals experience complications arising from soft tissue swelling and edema, or infection, resulting in exposure of test and control sites, and these animals are removed from the study. Four of the remaining animals are allowed healing times of 8 weeks, and three animals are sacrificed at 24 weeks following implantation.

Six of the seven control quadrants experience exposure of the sites between 4 days and two weeks post-operatively, and one control site remains covered for the 24 week time period the animal is in-life.

All seven of the remaining test sites remain covered for at least eight weeks following surgery. All test sites are very firm to palpation beginning about 2 weeks post surgery. In general there is a very slow decrease in the volume of tissue in test sites beginning about 6 weeks after surgery. This decrease is so slow as to be almost undetectable week by week. By 24 weeks the sites resume close to a pre-operative configuration.

Qualitative radiographic observations indicate substantial bone formation in test sites at 4 weeks post surgery. There is a general increase in density of bone over the 8 week and 24 week time periods. There is also a very slow decrease in bone height over time although in no cases does this progress below the cemento-enamel junction of the teeth. CT scans indicate some variability in new bone configuration, however, the scans do show substantial bone regeneration in the test sites. In general, the configuration of bone is not controlled as well as observed in Examples 3, 4, 5, and 6.

The single control site that remained covered for the 24 week period showed bone formation to within about 75% of the defect height of the teeth, although the bone between teeth did not reach this level. In general, there was substantially less bone formed in control sites compared to sites treated with TP PGA:TMC devices and rhBMP-2.

General Conclusions

To our knowledge, no one has before explained the biological, biomaterial, and biotechnology components necessary for this improved result, provided specifications for an device that will function to control generation of bone and periodontal tissue stimulated by TGF-J proteins, or reduced these teachings to practice.

What is claimed is:

1. A method of generating living bone having desired configuration in a mammal, said method comprising:

providing a tissue penetrable device comprising portions having a plurality of holes therethrough, wherein said holes permit cells and vascular structures to grow through said tissue penetrable device, said tissue penetrable device having mechanical properties that allow the device to be configured into a desired form and retained substantially in said desired form;

establishing a space with said tissue penetrable device in a mammal in such a way that a boundary is at least partially formed by said tissue penetrable device between said space and anatomical structures of said mammal surrounding said space, wherein said space has essentially the same conjuration as bone to be generated therein;

placing at least one TGF-Beta protein in said space;

allowing cells and blood vessels from said mammal to traverse said tissue penetrable device through said holes into said space; and generating bone in said space.

2. The method of claim 1 wherein said holes have diameters from about 3 microns to about 3,000 microns.

3. The method of claim 1 wherein said holes have diameters from about 50 microns to about 1,000 microns.

4. The method of claim 1 wherein said holes have diameters from about 150 microns to about 500 microns.

5. The method of claim 1 wherein said tissue penetrable device comprises a non-degradable material.

6. The method of claim 1 wherein said tissue penetrable device comprises a non-degradable material selected from the group consisting of polytetrafluoroethylene, perfluorinated polymers such as fluorinated ethylene propylene, silicone elastomer, polyurethane, polyethylene, polyethylene teraphthalate, polysulfone, non-degradable polycarboxylate, non-degradable polycarbonate, non-degradable polyester, polypropylene, polyacrylic, poly (hydroxymethacrylate), polymethylmethacrylate, and polyamide such as polyesteramide, and copolymers, block copolymers, and blends thereof.

7. The method of claim 1 wherein said tissue penetrable device comprises expanded polytetrafluoroethylene.

8. The method of claim 1 wherein said tissue penetrable device comprises a degradable material.

9. The method of claim 1 wherein said tissue penetrable device comprises a degradable material selected from the group consisting of non-highly cross-linked collagen, non-highly cross-linked hyaluronic acid, hydrolyzable polyester such as polylactic acid and polyglycolic acid, polyorthoester, degradable polycarbonate, degradable polycarboxylate, degradable polycaprolactone, polyanhydride and copolymers, block copolymers and blends thereof.

10. The method of claim 1 wherein said tissue penetrable device comprises a copolymer of polyglycolide/trimethylene carbonate.

11. The method of claim 1 wherein said tissue penetrable device is provided with reinforcement means.

12. The method of claim 11 wherein said reinforcement means comprises polypropylene mesh.

13. The method of claim 1 further comprising placing living cells in said space.

14. The method of claim 13 wherein said living cells comprises undifferentiated stem cells.

15. The method of claim 13 wherein said cells comprise cryopreserved cells.

16. The method of claim 1 further comprising providing said at least one TGF-J protein in a carrier substance.

17. The method of claim 16 wherein said carrier substance is selected from the group consisting of collagen, hyaluronic acid, calcium carbonate, tri-calcium phosphate, hydroxyapatite ceramic, magnesium sulfate, and polyester.

18. The method of claim 16 wherein said carrier substance comprises collagen.

19. The method of claim 16 wherein said carrier substance comprises hyaluronic acid.

20. The method of claim 1 further providing a matrix material within said space, said matrix material directing the functional structure of said desired living tissue generated.

21. The method of claim 1 wherein said TGF-Beta protein is selected from the group of TGF-Beta proteins consisting of TGF-Beta1, TGF-Beta2, BMP-2, BMP-1, BMP-3, BMP-4, BMP-5, BMP-6, BMP-7, BMP-8, BMP-9, BMP-10, BMP-11, BMP-12, BMP-13, BMP-15, Vgr-2, GDF-3, GDF-5, GDF-9, GDF-6, GDF-7, GDF-8, GDF-10, GDF-11, GDF-12, BIP, and MP52.

22. The method of claim 1 wherein said TGF-Beta protein is recombinant human Bone Morphogenetic Protein-2.

23. A method of generating living periodontal tissue having desired configuration in a mammal, said method comprising:

providing a tissue penetrable device comprising portions having a plurality of holes therethrough, wherein said holes permit cells and vascular structures to grow through said tissue penetrable device, said tissue penetrable device having mechanical properties that allow the device to be configured into a desired form and retained substantially in said desired form;

establishing a space with said tissue penetrable device in a mammal in such a way that a boundary is at least partially formed by said tissue penetrable device between said space and anatomical structures of said mammal surrounding said space, wherein said space has essentially the same configuration as periodontal tissue to be generated therein;

placing at least one TGF-Beta protein in said space;

allowing cells and blood vessels from said mammal to traverse said tissue penetrable device through said holes into said space; and generating periodontal tissue in said space.

24. The method of claim 23 wherein said holes have diameters from about 3 microns to about 3,000 microns.

25. The method of claim 23 wherein said holes have diameters from about 50 microns to about 1,000 microns.

26. The method of claim 23 wherein said holes have diameters from about 150 microns to about 500 microns.

27. The method of claim 23 wherein said tissue penetrable device comprises a non-degradable material.

28. The method of claim 23 wherein said tissue penetrable device comprises a non-degradable material selected from the group consisting of polytetrafluoroethylene, perfluorinated polymers such as fluorinated ethylene propylene, silicone, silicone rubber, polyurethane, polyethylene, polyethylene teraphthalate, polysulfone, non-degradable polycarboxylate, non-degradable polycarbonate, non-degradable polyester, polypropylene, polyacrylic, poly(hydroxymethacrylate), polymethylmethacrylate, and polyamide such as polyesteramide, and copolymers, block copolymers, and blends thereof.

29. The method of claim 23 wherein said tissue penetrable device comprises expanded polytetrafluoroethylene.

30. The method of claim 23 wherein said tissue penetrable device comprises a degradable material.

31. The method of claim 23 wherein said tissue penetrable device comprises a degradable material selected from the group consisting of non-highly cross-linked collagen, non-highly cross-linked hyaluronic acid, hydrolyzable polyesters such as polylactic acid and polyglycolic acid, polyorthoester, degradable polycarbonate, degradable polycarboxylate, degradable polycaprolactone, polyanhydride, and copolymers block copolymers, and blends thereof.

32. The method of claim 23 wherein said tissue penetrable device comprises a copolymer of polyglycolide/trimethylene carbonate.

33. The method of claim 23 wherein said tissue penetrable device is provided with reinforcement means.

34. The method of claim 33 wherein said reinforcement means comprises polypropylene mesh.

35. The method of claim 23 further comprising placing living cells in said space.

36. The method of claim 35 wherein said living cells are undifferentiated stem cells.

37. The method of claim 35 wherein said cells are cryopreserved cells.

38. The method of claim 23 further comprising providing said at least one TGF-J protein in a carrier substance.

39. The method of claim 38 wherein said carrier substance is selected from the group consisting of collagen, hyaluronic acid, calcium carbonate, tri-calcium phosphate, hydroxyapatite ceramic, magnesium sulfate, and polyester.

40. The method of claim 38 wherein said carrier substance is degradable.

41. The method of claim 38 wherein said carrier substance comprises collagen.

42. The method of claim 38 wherein said carrier substance comprises hyaluronic acid.

43. The method of claim 23 further providing a matrix material within said space, said matrix material directing the functional structure of said desired living tissue generated.

44. The method of claim 23 wherein said TGF-Beta protein is selected from the group of TGF-Beta proteins consisting of TGF-Beta1, TGF-Beta2, BMP-2 BMP-1, BMP-3, BMP-4, BMP-5, BMP-6, BMP-7, BMP-8, BMP-9, BMP-10, BMP-11, BMP-12, BMP-13, BMP-15, Vgr-2, GDF-3, GDF-5, GDF-9, GDF-6, GDF-7, GDF-8, GDF-10, GDF-11, GDF-12, BIP, and MP52.

45. The method of claim 23 wherein said TGF-Beta protein is recombinant human Bone Morphogenetic Protein-2.

46. A kit for generating living bone or periodontal tissue having desired configuration in a mammal, said kit comprising:
a tissue penetrable device comprising portions having a plurality holes therethrough, wherein said holes permit cells and vascular structures to grow through said tissue penetrable device, said tissue penetrable device having mechanical properties that allow the device to be configured into a desired shape and retained substantially in said desired shape; and
at least one TGF-Beta protein.

47. The kit of claim 46 wherein said holes have diameters from about 3 microns to about 3,000 microns.

48. The kit of claim 46 wherein said holes have diameters from about 50 microns to about 1,000 microns.

49. The kit of claim 46 wherein said holes have diameters from about 150 microns to about 500 microns.

50. The kit of claim 46 wherein said tissue penetrable device in comprised of a non-degradable material.

51. The kit of claim 46 wherein said tissue penetrable device comprises a non-degradable material selected from the group consisting of polytetrafluoroethylene, perfluorinated polymers such as fluorinated ethylene propylene, silicone, silicone rubber, polyurethane, polyethylene, polyethylene teraphthalate, polysulfone, non-degradable polycarboxylate, non-degradable polycarbonate, non-degradable polyester, polypropylene, polyacrylic, poly(hydroxymethacrylate), polymethylmethacrylate, and polyamide, and copolymers, block copolymers, and blends thereof.

52. The kit of claim 46 wherein said tissue penetrable device comprises expanded polytetrafluoroethylene.

53. The kit of claim 46 wherein said tissue penetrable device comprises a degradable material.

54. The kit of claim 46 wherein said tissue penetrable device comprises a degradable material selected from the group consisting of non-highly cross-linked collagen, non-highly cross-linked hyaluronic acid, hydrolyzable polyesters such as polylactic acid and polyglycolic acid, polyorthoesters, degradable polycarbonates, degradable polycarboxylates, degradable polycaprolactones, polyanhydrides and copolymers, block copolymers, and blends thereof.

55. The kit of claim 46 wherein said tissue penetrable device comprises a copolymer of polyglycolide/trimethylene carbonate.

56. The kit of claim 46 wherein said tissue penetrable device is provided with reinforcement means.

57. The kit of claim 46 wherein said reinforcement means comprises polypropylene mesh.

58. The kit of claim 46 further comprising cryopreserved cells.

59. The kit of claim 46 further comprising at least one TGF-Beta protein in a carrier substance.

60. The kit of claim 59 wherein wherein said carrier substance is selected from the group consisting of collagen, hyaluronic acid, calcium carbonate, tri-calcium phosphate, hydroxyapatite ceramic, magnesium sulfate, and polyester.

61. The kit of claim 59 wherein said carrier substance comprises collagen.

62. The kit of claim 59 wherein said carrier substance comprises hyaluronic acid.

63. The kit of claim 46 further providing a matrix material, said matrix material directing the functional structure of said desired living tissue generated.

64. The kit of claim 46 wherein said TGF-Beta protein is selected from the group of TGF-J proteins consisting of TGF-Beta1, TGF-Beta2, BMP-2 BMP-1, BMP-3, BMP-4, BMP-5, BMP-6, BMP-7, BMP-8, BMP-9, BMP-10, BMP-11, BMP-12, BMP-13, BMP-15, Vgr-2, GDF-3, GDF-5, GDF-9, GDF-6, GDF-7, GDF-8, GDF-10, GDF-11, GDF-12, BIP, and MP52.

65. The kit of claim 46 wherein said TGF-Beta protein is recombinant human Bone Morphogenic Protein-2.

* * * * *